US008041107B2

(12) United States Patent
Kato et al.

(10) Patent No.: US 8,041,107 B2
(45) Date of Patent: Oct. 18, 2011

(54) OVD (OPTICAL VARIABLE DEVICE) INSPECTION METHOD AND INSPECTION APPARATUS

(75) Inventors: Hisashi Kato, Odawara (JP); Shinichi Suzuki, Kawasaki (JP)

(73) Assignee: National Printing Bureau, Incorporated Administrative Agency, Tokyo-To (JP)

( * ) Notice: Subject to any disclaimer, the term of this patent is extended or adjusted under 35 U.S.C. 154(b) by 1260 days.

(21) Appl. No.: 11/661,936

(22) PCT Filed: Sep. 6, 2005

(86) PCT No.: PCT/JP2005/016310
§ 371 (c)(1),
(2), (4) Date: Mar. 6, 2007

(87) PCT Pub. No.: WO2006/028077
PCT Pub. Date: Mar. 16, 2006

(65) Prior Publication Data
US 2007/0258621 A1 Nov. 8, 2007

(30) Foreign Application Priority Data
Sep. 7, 2004 (JP) .................................. 2004-259785

(51) Int. Cl.
*G06K 9/00* (2006.01)
*G06K 15/00* (2006.01)
(52) U.S. Cl. ....... 382/152; 382/100; 382/141; 358/1.14; 283/88
(58) Field of Classification Search .................. 382/100, 382/152, 141; 358/1.14; 283/88
See application file for complete search history.

(56) References Cited

U.S. PATENT DOCUMENTS

| 3,882,454 | A | * | 5/1975 | Marie et al. ................... 382/199 |
| 4,099,971 | A | * | 7/1978 | Graube ............................. 430/1 |
| 4,483,124 | A | * | 11/1984 | Ohba et al. ........................ 53/54 |
| 4,945,215 | A | * | 7/1990 | Fukushima et al. ........... 235/457 |
| 5,463,649 | A | * | 10/1995 | Ashby et al. .................... 372/40 |
| 5,497,170 | A | * | 3/1996 | Kato et al. ......................... 345/9 |
| 5,966,456 | A | * | 10/1999 | Jones et al. .................... 382/135 |
| 5,995,303 | A | * | 11/1999 | Honguh et al. ................ 359/708 |
| 6,140,960 | A | * | 10/2000 | Kitayoshi ....................... 342/360 |
| 6,278,795 | B1 | * | 8/2001 | Anderson et al. ............. 382/135 |
| 6,282,308 | B1 | * | 8/2001 | Cossette ........................ 382/137 |
| 6,413,687 | B1 | * | 7/2002 | Hattori et al. ................... 430/10 |

(Continued)

FOREIGN PATENT DOCUMENTS

JP 10-078303 3/1998

(Continued)

*Primary Examiner* — Jason M Repko
*Assistant Examiner* — Mia M Thomas
(74) *Attorney, Agent, or Firm* — Birch, Stewart, Kolasch & Birch LLP

(57) ABSTRACT

A method and apparatus for inspecting defects and attachment position of an attached OVD without any influence of a change in the pattern of the OVD due to fluttering or undulation during conveyance of the printed product. Image input means and illumination means are arranged at positions where mirror reflected light and diffracted light from the OVD have values equal to or less than a threshold value upon a binarization process by image processing means. The image processing means executes the binarization process, compares the image data with the reference image data or the image data with the reference image data and the data indicating the reference position, and determines the acceptability of at least one of the form, area, and position of the OVD attached to the base material on the basis of a comparison result.

20 Claims, 12 Drawing Sheets

U.S. PATENT DOCUMENTS

| | | | |
|---|---|---|---|
| 6,427,020 B1* | 7/2002 | Rhoads | 382/100 |
| 6,447,979 B1* | 9/2002 | Hattori et al. | 430/270.1 |
| 6,490,089 B1* | 12/2002 | Fabiny | 359/571 |
| 6,608,911 B2* | 8/2003 | Lofgren et al. | 382/100 |
| 6,638,635 B2* | 10/2003 | Hattori et al. | 428/500 |
| 6,781,619 B1* | 8/2004 | Shirakura et al. | 348/46 |
| 6,782,115 B2* | 8/2004 | Decker et al. | 382/100 |
| 6,882,737 B2* | 4/2005 | Lofgren et al. | 382/100 |
| 6,900,767 B2* | 5/2005 | Hattori | 343/702 |
| 7,021,550 B2* | 4/2006 | Uchihiro et al. | 235/492 |
| 7,126,686 B2* | 10/2006 | Tsujita | 356/328 |
| 7,143,953 B2* | 12/2006 | Takahashi et al. | 235/494 |
| 7,278,586 B2* | 10/2007 | Takahashi et al. | 235/494 |
| 7,387,413 B2* | 6/2008 | Brinkmann et al. | 362/460 |
| 7,420,691 B2* | 9/2008 | Fukui | 356/632 |
| 7,437,000 B1* | 10/2008 | Rosenthal et al. | 382/173 |
| 7,583,821 B2* | 9/2009 | Xie et al. | 382/108 |
| 7,649,545 B2* | 1/2010 | Antonis | 348/92 |
| 7,710,579 B2* | 5/2010 | Yamaguchi et al. | 356/503 |
| 7,751,608 B2* | 7/2010 | Hersch et al. | 382/135 |
| 7,796,753 B2* | 9/2010 | Alasia et al. | 380/51 |
| 2002/0168513 A1* | 11/2002 | Hattori et al. | 428/336 |
| 2002/0196546 A1* | 12/2002 | Fabiny | 359/571 |
| 2003/0052084 A1* | 3/2003 | Tabery et al. | 216/59 |
| 2003/0205399 A1* | 11/2003 | Uchihiro et al. | 174/52.4 |
| 2003/0234294 A1* | 12/2003 | Uchihiro et al. | 235/492 |
| 2004/0129788 A1* | 7/2004 | Takahashi et al. | 235/492 |
| 2004/0252190 A1* | 12/2004 | Antonis | 348/92 |
| 2005/0000253 A1* | 1/2005 | Xie et al. | 65/417 |
| 2005/0052649 A1* | 3/2005 | Tsujita | 356/328 |
| 2005/0063562 A1* | 3/2005 | Brunk et al. | 382/100 |
| 2006/0237545 A1* | 10/2006 | Takahashi et al. | 235/492 |
| 2007/0145118 A1* | 6/2007 | Yoshida | 235/379 |
| 2007/0201720 A1* | 8/2007 | Rodriguez et al. | 382/100 |
| 2009/0033085 A1* | 2/2009 | Suto et al. | 283/67 |
| 2009/0302120 A1* | 12/2009 | Omura et al. | 235/492 |
| 2010/0060551 A1* | 3/2010 | Sugiyama et al. | 345/8 |

FOREIGN PATENT DOCUMENTS

| | | |
|---|---|---|
| JP | 2000-187008 | 7/2000 |
| JP | 2001-256530 A | 9/2001 |
| JP | 2002-181718 | 6/2002 |
| JP | 2002-221497 A | 8/2002 |
| JP | 2004-35014 A | 2/2004 |

* cited by examiner

OVD (OPTICAL VARIABLE DEVICE) INSPECTION METHOD AND INSPECTION APPARATUS

TECHNICAL FIELD

The present invention relates to an inspection method and inspection apparatus for an OVD attached to a base material such as a bank note, securities, merchandise coupon, or card.

BACKGROUND ART

An OVD (Optical Variable Device) is a foil formed by depositing a metal on a relief diffraction grating and has a unique optical change function such as three-dimensional image formation or color shift. The OVD is called a hologram or metal foil. There are a sheet type OVD made by die-cutting a sheet, a patch type OVD formed into a predetermined shape, and a linear thread type OVD. The OVDs are attached to a partial or entire surface of a valuable printed product such as a bank note, securities, merchandise coupon, or credit card and used as one of anti-counterfeit technologies because of their advanced manufacturing methods.

A printed product with an OVD is manufactured by attaching a sheet- or patch-type hologram to a base material by transfer or press. A thread-type OVD is contained in a base material as a watermark or attached into or onto a sheet surface by transfer or press.

In manufacturing products with OVD, defects such as a pinhole or peeling may occur upon attaching a hologram sheet to a base material due to, e.g., a hologram sheet print error, a transfer error to a base material, or maladjustment of machines. OVD attachment state inspection is an important item of quality control. It is necessary to remove a product with a defect as a defective. However, the pattern observed on the diffraction grating of an OVD changes depending on a slight change in the incident angle of light because the diffraction grating has a dependence on the wavelength and incident angle of light. It is therefore impossible to inspect a stable OVD attachment state under visible light. An inspection method or apparatus places a printed product with an OVD, acquires its image by using a camera, and executes comparison testing by displaying the image on a monitor or printing the image.

An inspection apparatus is known, which reproduces, captures, and inspects a hologram image of a holographic printed product containing a holographic region and a print region (e.g., patent reference 1).

A hologram position inspection method and apparatus are also used as an inspection method and apparatus capable of easily detecting an edge of a hologram and easily inspecting whether the hologram is applied within a tolerance (e.g., patent reference 2).

There also exist a hologram sheet inspection method and apparatus capable of automatically accurately inspecting many different kinds of holograms in a large quantity at once and continuously for each of error items including chipping of a sheet, hologram image misregistration, and unprinted areas, repetitive printing, and misregistration of hologram sheets (e.g., patent reference 3).

Patent reference 1: Japanese Patent Laid-Open No. 2000-187008

Patent reference 2: Japanese Patent No. 3095215

Patent reference 3: Japanese Patent Laid-Open No. 2002-181718

DISCLOSURE OF INVENTION

In the inspection method of the above-described inspection apparatus, the reflecting layer of a reflective hologram strongly regularly reflects irradiation light from an irradiation means. An image capturing means receives the reflected light so that the image is discriminated on the basis of the difference between the hologram region and other regions. If an image of regularly reflected light of irradiation light is captured, the image exhibits strong reflection at some parts depending on the irradiation light amount. This may make it impossible to extract a form defect such as a hologram edge or pinhole because of blur.

In the above-described hologram position inspection method and apparatus, the position of a hologram placed on a transparent plate is inspected by arranging an inspection plate such as a shielding plate so that diffraction occurs within the position tolerance in the visible light range. That is, the OVD pattern is extracted in the visible light range where a slight change in the angle changes the pattern. For this reason, the method and apparatus are not adaptable when the base material with an OVD is a flexile medium such as a paper sheet because it is readily influenced by fluttering, angle, and undulation.

The above-described hologram sheet inspection method and apparatus segment an image obtained by capturing a hologram sheet into a number of blocks, and recognize a defective portion formed on an edge of the design part of the hologram sheet on the basis of a difference image obtained by pattern matching between the captured image and a reference image containing the minimum and maximum values of each block. If the base material has a uniform flat surface, like a plate-shaped card, the method and apparatus are suitably used to extract an edge. However, the surface of a base material such as a paper sheet to which the present invention is applied readily undulates as compared to a card, and the angle changes due to, e.g., slight fluttering that occurs during conveyance. It is therefore difficult to extract a defect of an OVD form.

As described above, when a printed product with an OVD is input in the visible light range, the glossy pattern of the OVD changes as shown in FIG. 1A or 1B depending on a slight change in the incident angle or the state of the print material. For this reason, stable OVD inspection by form comparison such as pattern matching is impossible because defect extraction becomes unusable in accordance with the change in the glossy pattern. In addition, the boundary between the print material and the OVD becomes indistinct due to the change in the glossy pattern. Hence, the process of extracting an OVD form from an image line part of the printed pattern is complex.

It is an object of the present invention to provide an OVD inspection method and inspection apparatus capable of causing an optical device to inspect the position of an OVD and attachment defects such as burrs, chipping, fractures, pinholes, malformation, and perforation in an OVD without any influence of a change in the pattern of the OVD image due to a change in the angle caused by fluttering or undulation during conveyance upon capturing the attachment state of the OVD attached to a printed product of a base material such as a paper sheet, unlike the conventional techniques.

According to the present invention, there is provided an OVD inspection method of inspecting an OVD attached to a base material by using an inspection apparatus including illumination means, image input means including image capturing means, storage means, and image processing means, comprising:

arranging the image capturing means and the illumination means at positions where mirror-reflected light and diffracted light from a region of the OVD in a wave range not less than 650 [nm] have values not more than a threshold value upon a binarization process by the image processing means;

causing the illumination means to irradiate a surface of the base material with infrared rays or light containing infrared rays;

causing the image input means to input image data including a wave range not less than 650 [nm] from a region including the OVD attached to the base material;

causing the storage means to store, in advance, reference image data of an OVD serving as a standard, or the reference image data and reference data indicating a reference position of the OVD serving as the standard; and causing the image processing means to execute the binarization process of the input image data, compare the binarized image data with the reference image data, or the binarized image data with the reference image data and the reference data, and determine acceptability of at least one of a form, area, and position of the OVD attached to the base material on the basis of a comparison result.

According to the present invention, there is provided an OVD inspection method of inspecting an OVD attached to a base material by using an inspection apparatus including illumination means, image input means including image capturing means, storage means, and image processing means, comprising:

arranging the image capturing means and the illumination means at positions where mirror-reflected light and diffracted light from a region of the OVD in a wave range not less than 650 [nm] have values not more than a threshold value upon a binarization process by the image processing means;

causing the illumination means to irradiate a surface of the base material with infrared rays or light containing infrared rays;

causing the image input means to input image data including a wave range not less than 650 [nm] from a region including the OVD attached to the base material;

causing the storage means to store outline data indicating an outline of an OVD serving as a standard in advance; and causing the image processing means to execute the binarization process of the input image data, extract outline data of the OVD attached to the base material from the image data and compare the extracted outline data with the outline data of the OVD serving as the standard, and determine acceptability of a form of the OVD attached to the base material on the basis of a comparison result.

Further, according to the present invention, there is provided an OVD inspection method of inspecting an OVD attached to a base material by using an inspection apparatus including illumination means, image input means including image capturing means, storage means, and image processing means, comprising:

arranging the image capturing means and the illumination means at positions where mirror-reflected light and diffracted light from a region of the OVD in a wave range not less than 650 [nm] have values not more than a threshold value upon a binarization process by the image processing means;

causing the illumination means to irradiate a surface of the base material with infrared rays or light containing infrared rays;

causing the image input means to input image data including a wave range not less than 650 [nm] from a region including the OVD attached to the base material;

causing the storage means to store reference data indicating an area value of an OVD serving as a standard in advance; and causing the image processing means to execute the binarization process of the input image data, calculate an area value of the OVD attached to the base material from the image data and compare the calculated area value with the area value indicated by the reference data of the OVD serving as the standard, and determine acceptability of an attachment state of the OVD on the basis of a comparison result.

Further, according to the present invention, there is provided an OVD inspection method of inspecting an OVD attached to a base material by using an inspection apparatus including illumination means, image input means including image capturing means, storage means, and image processing means, comprising:

arranging the image capturing means and the illumination means at positions where mirror-reflected light and diffracted light from a region of the OVD in a wave range not less than 650 [nm] have values not more than a threshold value upon a binarization process by the image processing means;

causing the illumination means to irradiate a surface of the base material with infrared rays or light containing infrared rays;

causing the image input means to input image data including a wave range not less than 650 [nm] from a region including the OVD attached to the base material;

causing the storage means to store, in advance, coordinates representing a position of an OVD and coordinates indicating a reference position to detect the position of the OVD when an OVD serving as a standard is attached to the base material; and causing the image processing means to execute the binarization process of the input image data, calculate, from the image data, coordinates indicating a position of the OVD attached to the base material and a reference position to detect the position of the OVD and compare the position of the OVD attached to the base material and the reference position to detect the position of the OVD with the coordinates representing the position of the OVD and the coordinates indicating the reference position to detect the position of the OVD when the OVD serving as the standard is attached to the base material, and determine acceptability of the position of the OVD on the basis of a comparison result.

Further, according to the present invention, there is provided an OVD inspection method of inspecting an OVD attached to a base material by using an inspection apparatus including illumination means, image input means including image capturing means, storage means, and image processing means, comprising:

arranging the image capturing means and the illumination means at positions where mirror-reflected light and diffracted light from a region of the OVD in a wave range not less than 650 [nm] have values not more than a threshold value upon a binarization process by the image processing means;

causing the illumination means to irradiate a surface of the base material with infrared rays or light containing infrared rays;

causing the image input means to input image data including a wave range not less than 650 [nm] from a region including the OVD attached to the base material and a reference mark to detect a position of the OVD;

causing the storage means to store, in advance, coordinates representing a position of an OVD and coordinates representing a reference mark to detect the position of the OVD when an OVD serving as a standard is attached to the base material; and causing the image processing means to execute the binarization process of the input image data, calculate, from the image data, coordinates representing a position of the OVD attached to the base material and a position of the reference mark and compare the coordinates representing the position of the OVD attached to the base material and the position of the reference mark with the coordinates representing the position of the OVD and the coordinates representing the reference mark to detect the position of the OVD when the OVD serving as the standard is attached to the base material, and determine acceptability of the position of the OVD on the basis of a comparison result.

Further, according to the present invention, there is provided an OVD inspection method of inspecting an OVD attached to a base material by using an inspection apparatus including illumination means, image input means including image capturing means, storage means, and image processing means, comprising:

arranging the image capturing means and the illumination means at positions where mirror-reflected light and diffracted light from a region of the OVD in a wave range not less than 650 [nm] have values not more than a threshold value upon a binarization process by the image processing means;

causing the illumination means to irradiate a surface of the base material with infrared rays or light containing infrared rays;

causing the image input means to input image data including a wave range not less than 650 [nm] from a region including the OVD attached to the base material and a portion representing a position of the base material;

causing the storage means to store, in advance, coordinates representing a position of an OVD and coordinates representing the base material when an OVD serving as a standard is attached to the base material; and causing the image processing means to execute the binarization process of the input image data, calculate, from the image data, coordinates representing the OVD attached to the base material and coordinates representing the base material and compare the coordinates representing the OVD attached to the base material and the coordinates representing the base material with the coordinates representing the position of the OVD and the coordinates representing the base material when the OVD serving as the standard is attached to the base material, and determine acceptability of the position of the OVD on the basis of a comparison result.

According to the present invention, there is provided an OVD inspection apparatus for inspecting an OVD attached to a base material, comprising:

illumination means having a light source to irradiate the base material with the OVD with light containing infrared rays;

image input means for inputting image data including a wave range not less than 650 [nm] from a region including the OVD attached to the base material irradiated with the light containing infrared rays from said illumination means, said image input means including image capturing means which is arranged, relative to said illumination means, at a position where mirror-reflected light and diffracted light from the region of the OVD in a wave range not less than 650 [nm] have values not more than a threshold value upon a binarization process by image processing means;

storage means for storing, in advance, reference image data of an OVD serving as a standard or the reference image data and reference data indicating a reference position of the OVD serving as the standard; and image processing means for executing the binarization process of the input image data, comparing the binarized image data with the reference image data, or comparing the binarized image data with the reference image data and the reference data, and determining acceptability of at least one of a form, area, and position of the OVD attached to the base material on the basis of a comparison result.

According to the present invention, there is provided an OVD inspection apparatus for inspecting an OVD attached to a base material, comprising:

illumination means having a light source to irradiate the base material with the OVD with light containing infrared rays;

image input means for inputting image data including a wave range not less than 650 [nm] from a region including the OVD attached to the base material irradiated with the light containing infrared rays from said illumination means, said image input means including image capturing means which is arranged, relative to said illumination means, at a position where mirror-reflected light and diffracted light from the region of the OVD in a wave range not less than 650 [nm] have values not more than a threshold value upon a binarization process by image processing means;

storage means for storing outline data indicating an outline of an OVD serving as a standard in advance; and image processing means for executing the binarization process of the input image data, extracting outline data of the OVD attached to the base material from the image data and comparing the extracted outline data with the outline data of the OVD serving as the standard, and determining acceptability of a form of the OVD attached to the base material on the basis of a comparison result.

According to the present invention, there is provided an OVD inspection apparatus for inspecting an OVD attached to a base material, comprising:

illumination means having a light source to irradiate the base material with the OVD with light containing infrared rays;

image input means for inputting image data including a wave range not less than 650 [nm] from a region including the OVD attached to the base material irradiated with the light containing infrared rays from said illumination means, said image input means including image capturing means which is arranged, relative to said illumination means, at a position where mirror-reflected light and diffracted light from the region of the OVD in a wave range not less than 650 [nm] have values not more than a threshold value upon a binarization process by image processing means;

storage means for storing area data indicating an area of an OVD serving as a standard in advance; and image processing means for executing the binarization process of the input image data, extracting area data of the OVD attached to the base material from the image data and comparing the area data with the area data of the OVD serving as the standard, and determining acceptability of an attachment state of the OVD attached to the base material on the basis of a comparison result.

According to the present invention, there is provided an OVD inspection apparatus for inspecting an OVD attached to a base material, comprising:

illumination means having a light source to irradiate the base material with the OVD with light containing infrared rays;

image input means for inputting image data including a wave range not less than 650 [nm] from a region including the OVD attached to the base material irradiated with the light containing infrared rays from said illumination means, said image input means including image capturing means which is arranged, relative to said illumination means, at a position where mirror-reflected light and diffracted light from the region of the OVD in a wave range not less than 650 [nm] have values not more than a threshold value upon a binarization process by image processing means;

storage means for storing, in advance, coordinate data indicating coordinates representing a position of an OVD and coordinates indicating a reference position to detect the position of the OVD when an OVD serving as a standard is attached to the base material; and image processing means for executing the binarization process of the input image data, calculating, from the image data, coordinates indicating a position of the OVD attached to the base material and a reference position to detect the position of the OVD and comparing the position of the OVD attached to the base material and the reference position to detect the position of the OVD with the coordinates representing the position of the OVD and the coordinates indicating the reference position to detect the position of the OVD when the OVD serving as the standard is attached to the base material, and determining acceptability of the position of the OVD attached to the base material on the basis of a comparison result.

According to the present invention, there is provided an OVD inspection apparatus for inspecting an OVD attached to a base material, comprising:

illumination means having a light source to irradiate the base material with the OVD with light containing infrared rays;

image input means for inputting image data including a wave range not less than 650 [nm] from a region including the OVD attached to the base material irradiated with the light containing infrared rays from said illumination means, said image input means including image capturing means which is arranged, relative to said illumination means, at a position where mirror-reflected light and diffracted light from the region of the OVD in a wave range not less than 650 [nm] have values not more than a threshold value upon a binarization process by image processing means;

storage means for storing, in advance, coordinate data indicating coordinates representing a position of an OVD and coordinates representing a position of a reference mark to detect the position of the OVD when an OVD serving as a standard is attached to the base material; and image processing means for executing the binarization process of the input image data, calculating, from the image data, coordinates representing a position of the OVD attached to the base material and the coordinates of a position of the reference mark and comparing the coordinates representing the position of the OVD attached to the base material and the coordinates representing the position of the reference mark with the coordinates of a position representing the OVD and the coordinates representing the position of the reference mark to detect the position of the OVD when the OVD serving as the standard is attached to the base material, and determining acceptability of the position of the OVD attached to the base material on the basis of a comparison result.

According to the present invention, there is provided an OVD inspection apparatus for inspecting an OVD attached to a base material, comprising:

illumination means having a light source to irradiate the base material with the OVD with light containing infrared rays;

image input means for inputting image data including a wave range not less than 650 [nm] from a region including the OVD attached to the base material irradiated with the light containing infrared rays from said illumination means, said image input means including image capturing means which is arranged, relative to said illumination means, at a position where mirror-reflected light and diffracted light from the region of the OVD in a wave range not less than 650 [nm] have values not more than a threshold value upon a binarization process by image processing means;

storage means for storing, in advance, coordinate data indicating coordinates representing a position of an OVD and coordinates representing a position of the base material when an OVD serving as a standard is attached to the base material; and image processing means for executing the binarization process of the input image data, calculating, from the image data, coordinates representing a position of the OVD attached to the base material and coordinates of a position representing the base material and comparing the coordinates representing the position of the OVD attached to the base material and the coordinates of the position representing the base material with the coordinates of a position representing the OVD and the coordinates of the position representing the base material when the OVD serving as the standard is attached to the base material, and determine acceptability of the position of the OVD attached to the base material on the basis of a comparison result.

Here, in the above OVD inspection method, said illumination means and said image capturing means may be arranged such that an angle $\phi$ between said illumination means and said image capturing means, a wavelength $\lambda$ [nm] of the light emitted from said illumination means, and the number N (N≧1) of trenches per 1 [mm] in the OVD hold a relationship given by $\sin\phi < N\lambda \text{[nm]} \times 10^{-6}$ in the region of the OVD attached to the base material.

In the above OVD inspection apparatus, said illumination means and said image capturing means may be arranged such that an angle $\phi$ between said illumination means and said image capturing means, a wavelength $\lambda$ [nm] of the light emitted from said illumination means, and the number N (N≧1) of trenches per 1 [mm] in the OVD hold a relationship given by $\sin\phi < N\lambda \text{[nm]} \times 10^{-6}$ in the region of the OVD attached to the base material.

The surface of the applied OVD is considerably flat. Reflected light contains a mirror-reflected light component and a diffracted light component. In acquiring the image of the OVD region, when the influence of mirror-reflected light and diffracted light from the OVD is eliminated, the contrast of infrared transmitting characteristic from the printed product around the OVD can be used. In this way, the form of the OVD, partial defects, and position accuracy can be evaluated. Especially even when the printed product with the OVD is conveyed at a high speed, and the print base material slightly floats, flutters, or undulates during conveyance, it is possible to always stably acquire the image data of the OVD form by using infrared rays that hardly generate diffracted light as compared to visible light. Hence, online complete inspection of OVD attachment quality can be done accurately.

Even in a resting state, it is possible to input and inspect the image data of the OVD.

The present invention is applicable not only to a stripe- and patch-type holograms but also to a thread-type hologram.

DESCRIPTION OF THE REFERENCE NUMERALS

| | |
|---|---|
| 1 | CCD area sensor camera with visible light cutting infrared transmitting filter |
| 2 | light source |
| 3 | printed product |
| 4 | OVD |
| 5, 12 | image input means |
| 6, 13 | image processing means |
| 6a | calculation unit |
| 6b | determination unit |
| 7 | CCD line sensor camera with visible light cutting infrared transmitting filter |
| 8 | linear light source |
| 9 | inspection cylinder |
| 10, 20 | input unit |
| 14 | reference mark |
| 15 | pattern on surface of printed product |
| 21 | output means |
| 22 | storage means |

BEST MODE FOR CARRYING OUT THE INVENTION

An embodiment of the present invention will be described.

Figure 2:
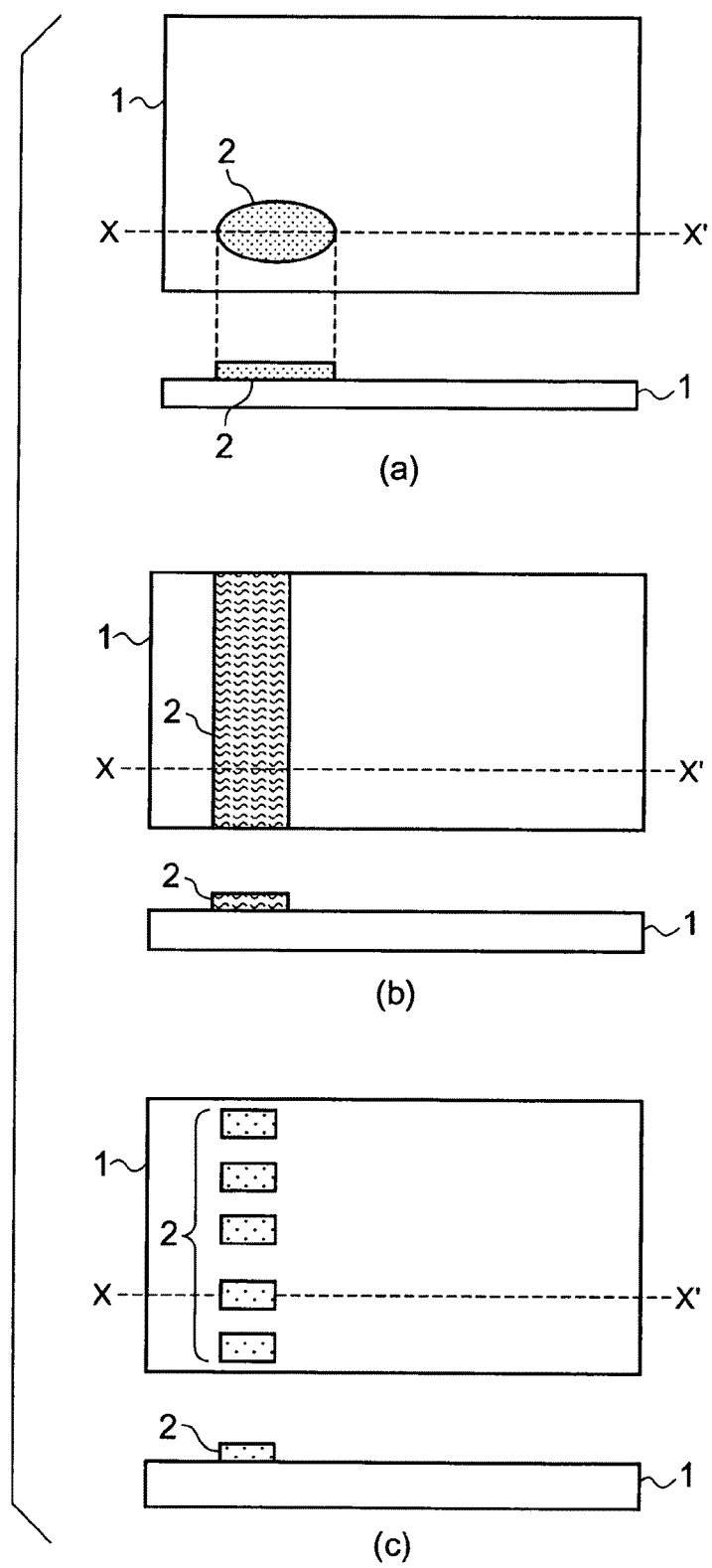
FIG. 2(a) to 2(c) are explanatory views showing printed products with different OVDs.

An OVD inspection method and apparatus according to the embodiment can inspect, e.g., any one of a patch-type OVD 4a attached onto a base material 1 of a printed product 3 as shown in FIG. 2(a), a stripe-type OVD 4b as shown in FIG. 2(b), and a thread-type OVD 4c as shown in FIG. 2(c).

Preferably, the OVD is a printed pattern using infrared transmission ink or is attached onto a base material that reflects infrared rays so that the image of the OVD can be acquired more clearly.

Figure 3:
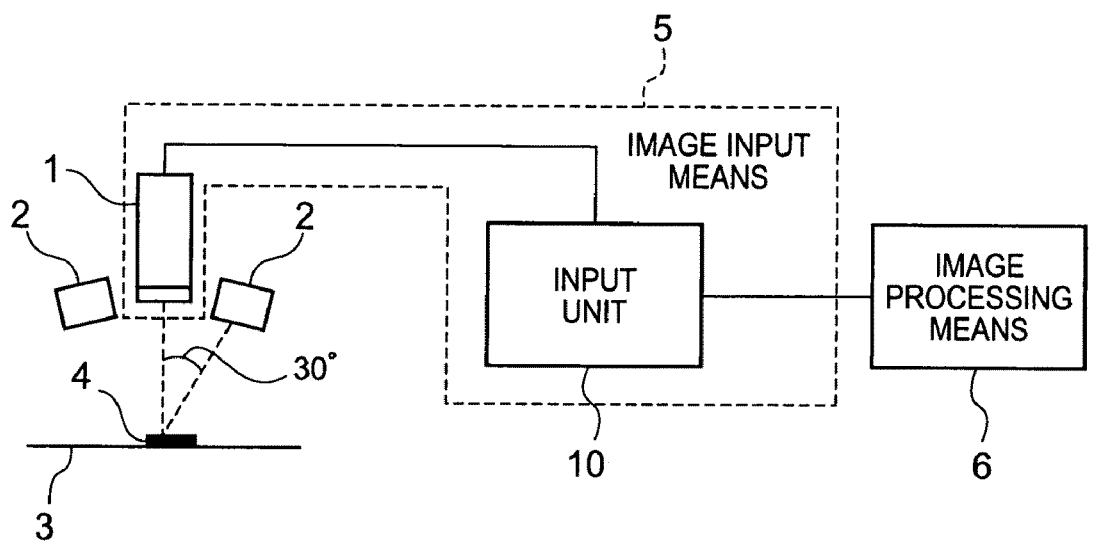
FIG. 3 is a schematic view showing the arrangement of an apparatus for inspecting an OVD offline according to the embodiment of the present invention.

To inspect the OVD 4 attached to the printed product 3, the inspection apparatus used to execute the OVD inspection method according to the embodiment comprises an image input means 5 including a camera 1 serving as an image capturing means and an input unit 10 which inputs image data captured by the camera 1, a light source 2 serving as an irradiation means, and an image processing means 6 for executing a predetermined process for received image data, as shown in FIG. 3.

The camera 1 is an image capturing means. A CCD area sensor camera with a visible light cutting infrared transmitting filter which removes the visible light range with a wavelength shorter than 650 [nm] and transmits the infrared range with a wavelength of 650 [nm] or more is used.

The camera 1 is preferably arranged perpendicular to an inspection target, i.e., an OVD 4 to avoid any distortion in its image.

The light source 2 is an illumination means. The light source 2 preferably irradiates the OVD 4 obliquely because mirror-reflected light from the region of the OVD 4 must not largely influence the camera 1. More specifically, the mirror-reflected light must have a predetermined light intensity or less. The light source 2 is installed at such a position that the mirror-reflected light obtains a threshold value or less upon, e.g., a binarization process by the image processing means 6. However, if the irradiation direction is too close to a direction parallel to the OVD 4, the light-receiving amount decreases. The light source 2 needs to be installed in consideration of this as well.

It is also indispensable to set the light source 2 at such a position that diffracted light generated from the OVD 4 rarely affects the camera 1. The power of diffracted light generated from the OVD 4 has directivity. Hence, it is preferable to arrange the light source 2 with respect to the inspection target, i.e., the OVD 4 to minimize the diffracted light. To prevent the camera 1 from receiving the diffracted light from the OVD 4 as much as possible, the light intensity of the diffracted light must have a predetermined value or less, and for this purpose, the light source 2 is installed at such a position that the diffracted light obtains a threshold value or less upon, e.g., a binarization process by the image processing means 6.

Figure 4:
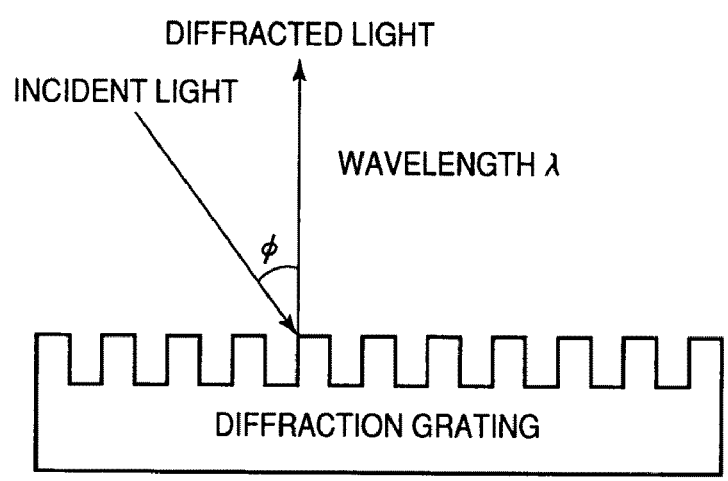
FIG. 4 is an explanatory view showing the angle between diffracted light and incident light with a wavelength λ, to a diffraction grating.

Alternatively, the diffraction grating of the OVD 4, i.e., the inspection target and the camera 1 need to be arranged such that a relationship given by $\sin \phi < N\lambda \times 10^{-6}$ holds, where φ is the angle of incident light from the light source 2, λ is the wavelength of the incident light, and N (N≧1) is the number of trenches per 1 [mm] in the diffraction grating, as shown in FIG. 4. In addition, it is essential to arrange the light source 2 in a direction to inhibit the light source 2 from receiving mirror-reflected light, as described above.

Figure 5:
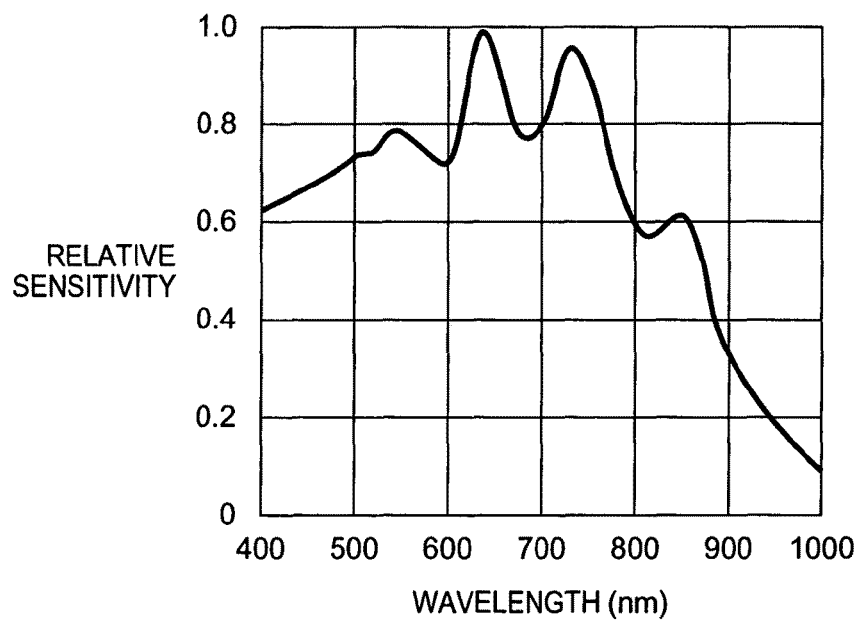
FIG. 5 is a graph showing an example of the spectral sensitivity of a CCD area sensor camera used in the OVD inspection apparatus according to the embodiment.
Figure 6:
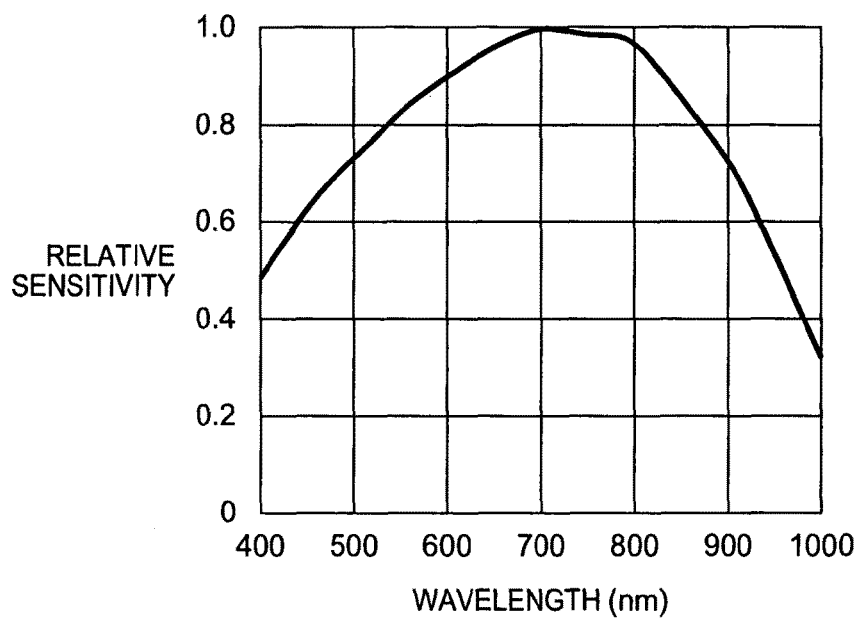
FIG. 6 is a graph showing an example of the spectral sensitivity of a CCD line sensor camera used in the OVD inspection apparatus according to the embodiment.

Examples of the camera 1 is a CCD line sensor camera and a CCD area sensor camera. As a functional characteristic, the camera 1 must have a relatively high spectral sensitivity in the infrared range with a wavelength of 650 [nm] or more as shown in FIG. 5 or 6.

A CCD line sensor camera is suitable for capturing the image of the OVD 4 during conveyance of the printed product 3. One-dimensional images of a region including the OVD 4 attached to the printed product 3 are sequentially acquired by a CCD line sensor camera, thereby generating a two-dimensional image.

On the other hand, a CCD area sensor camera capable of capturing a two-dimensional image is suitable for image capturing of the printed product 3 at rest.

Figure 7:
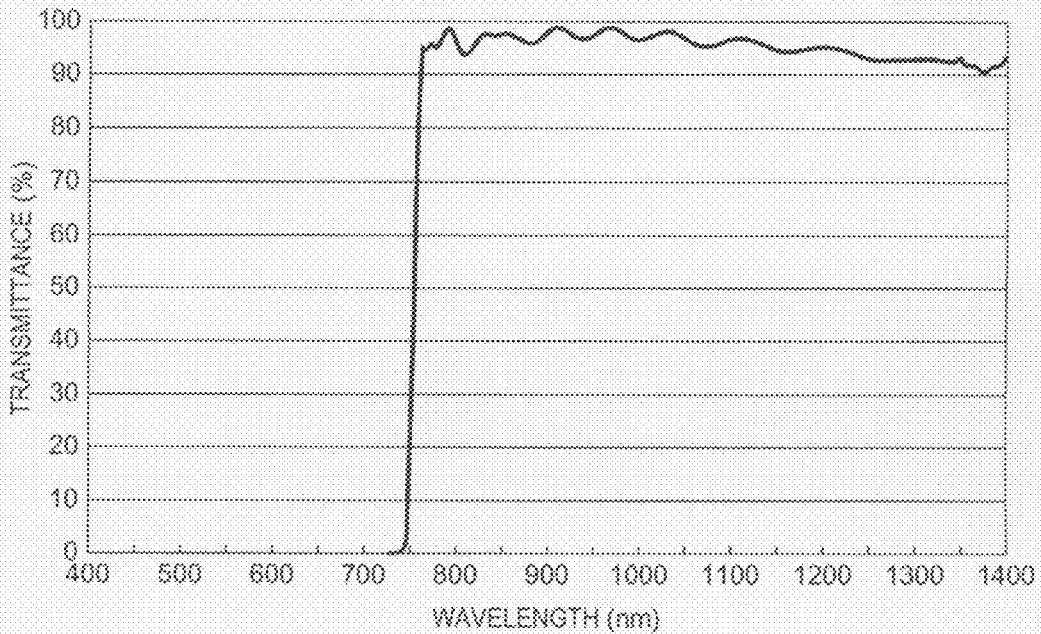
FIG. 7 is a graph showing the spectral transmittance of a visible light cutting infrared transmitting filter in the OVD inspection apparatus according to the embodiment.

The camera can have, at its lens portion, a filter which removes visible light with a wavelength shorter than 750 [nm] and passes light in the infrared range with a wavelength of 750 [nm] or more, as shown in FIG. 7.

Figure 8:
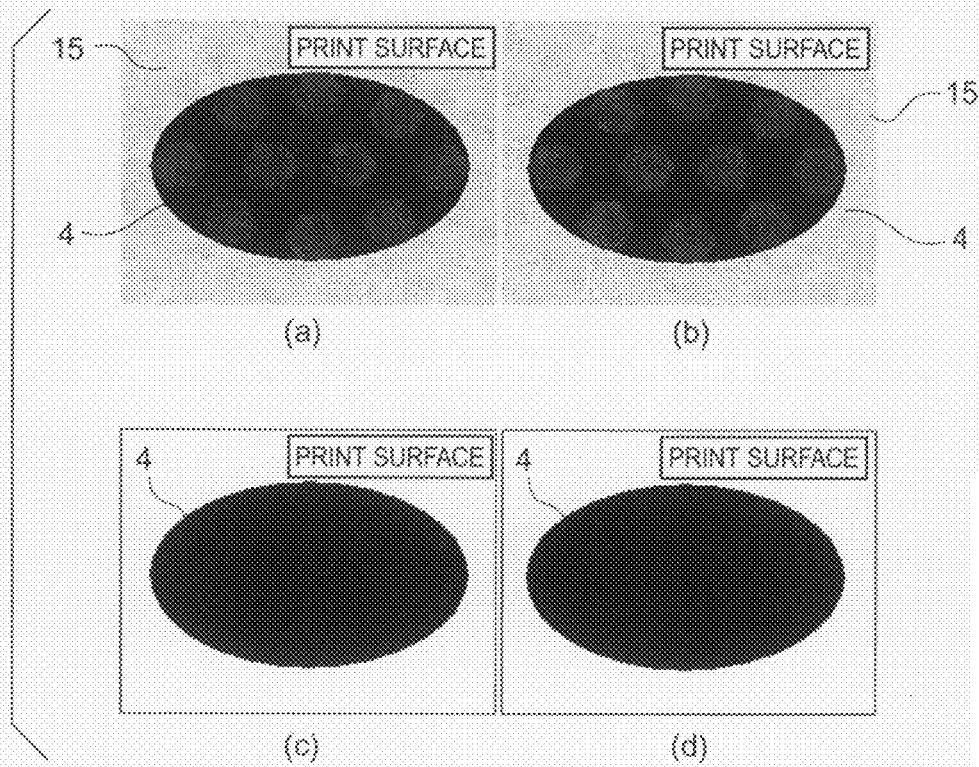
FIG. 8(a) to 8(d) are explanatory views showing images of a printed product with an OVD which are acquired in the infrared range.

This makes it possible to cut reflected light in the visible light range so as to avoid any change in the image related to the form of the OVD 4 and acquire stable image data, as shown in FIG. 8(a) or 8(b).

Almost the same effect is available by using a filter which removes light in a wave range shorter than not 750 [nm] but 650 [nm] and a range of 650 [nm] or more.

An OVD image obtained by capturing the region including the OVD 4 attached to the printed product 3 is a monochrome image that is very useful for inspecting the OVD attachment state, as shown in FIG. 8(c) or 8(d), unlike an image obtained using visible light, i.e., a reflected image with a changeable OVD surface. This image facilitates extraction of an OVD edge or form. Hence, it is easy to extract and confirm attachment defects such as burrs, chipping, fractures, pinholes, malformation, and perforation.

Figure 1:
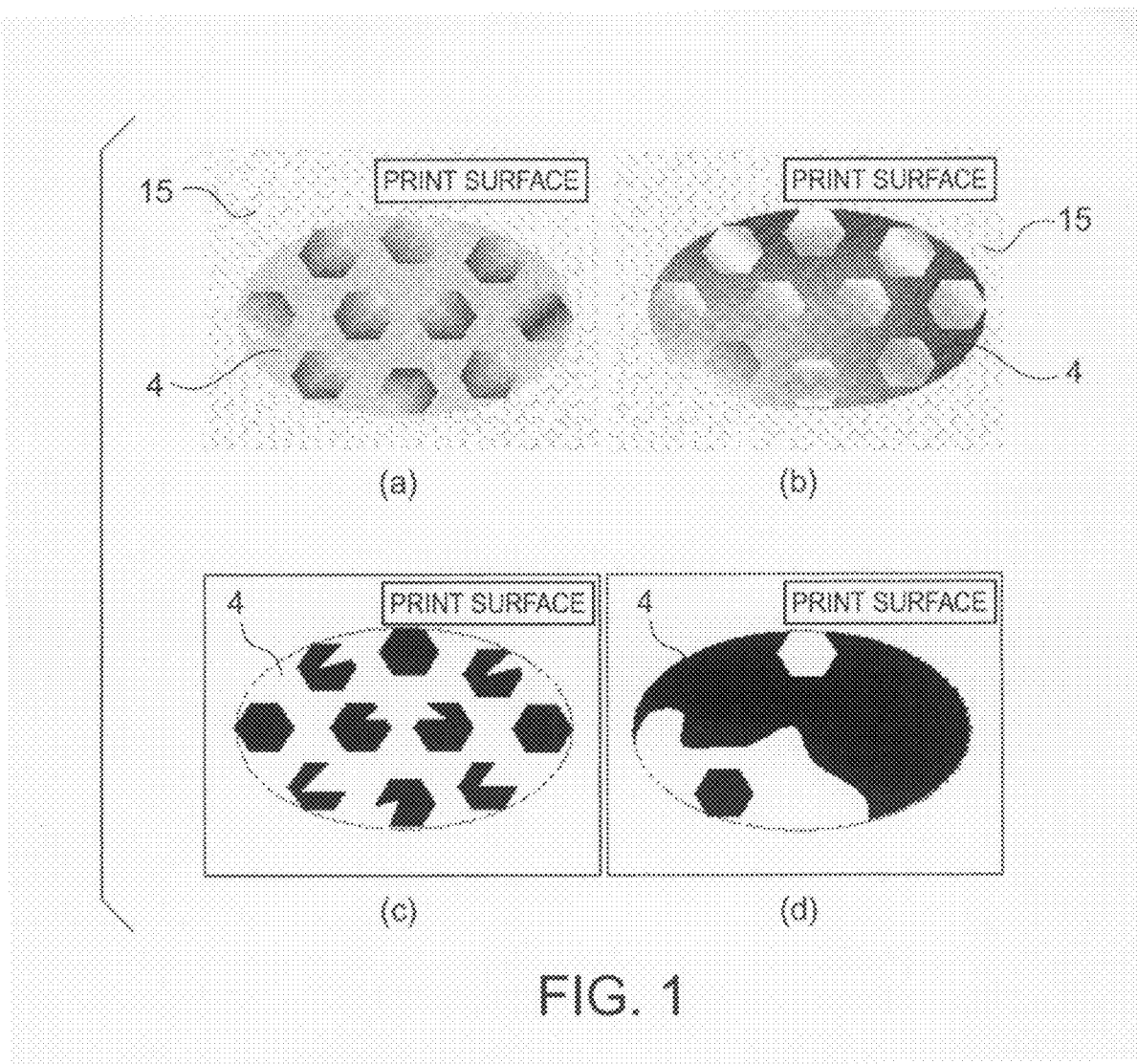
FIG. 1(a) to 1(d) are explanatory views showing images of a printed product with an OVD which are acquired in the visible light range.

The method and principle of OVD image data acquisition will be described in more detail. Conventional image data acquisition using visible light is suitable for acquiring a changing pattern image in an OVD because reflected light from the OVD is used. However, this technique is inappropriate for quality inspection in manufacturing, i.e., checking the quality and position during the process of attaching an OVD to a printed product using a flexible medium such as a paper sheet as a base material. For example, when image data in the region including the OVD is acquired by using light in the visible light range, the image shown in FIG. 1(a) is obtained, as described above. FIG. 1(b) shows an image obtained by changing the pattern in the OVD by changing the angle of the same OVD region.

As is apparent from FIGS. 1(a) and 1(b), even in a single OVD with a certain design, captured image data changes depending on the reflection of visible light because the pattern image in the OVD changes.

When the acquired OVD images undergo binarization as a general image process, images shown in FIGS. 1(c) and 1(d) are obtained. In binarization, a target is extracted from an image, and the background and graphic pattern are separated to analyze the characteristic feature of the image. More specifically, a grayscale image with a density value is converted into an image expressed by two values, 0 and 1. The images shown in FIGS. 1(c) and 1(d) are obtained by replacing bright portions with white and dark portions with black by the binarization process.

An auxiliary line indicated by a broken line represents the OVD edge of the OVD region. These images are obtained by executing the binarization process for the same OVD whose internal pattern has changed due to a change in the observation angle or illumination angle.

Even in the same OVD, the resultant images shown in FIGS. 1(c) and 1(d) exhibit different patterns in the visible light range as if they were acquired from different OVDs. If strong reflection takes place at the boundary between the OVD and the paper surface, some kinds of changeable pattern images make it very difficult to determine whether the image obtained by reflection represents an OVD edge or discontinuity caused by chipping, as shown in FIG. 1(d).

If the base material with the OVD is a card, image data can be obtained by strictly setting the angle and position of the camera and irradiation. However, if a paper sheet as a flexible medium is irradiated with a light source in the visible light range, slight fluttering during conveyance changes the angle, and in turn, the exhibited image even when the light source position does not change. This method is therefore inappropriate for inspection.

In this embodiment, the region including the OVD is irradiated with infrared rays or illumination containing infrared rays, and an image is extracted. If the region is irradiated with infrared rays or illumination containing infrared rays from a direction to minimize the influence of mirror-reflected light and diffracted light, a clear OVD image can be extracted because of the contrast under the infrared rays.

In many cases, an OVD has a plurality of diffraction directions. This limits the irradiation angle of illumination to the camera and inspection target. In the diffraction grating of an OVD, the reflection angle of visible light has a range a in FIG. 9. On the other hand, the reflection angle of infrared rays has a range β outside the angle range α.

Figure 9:
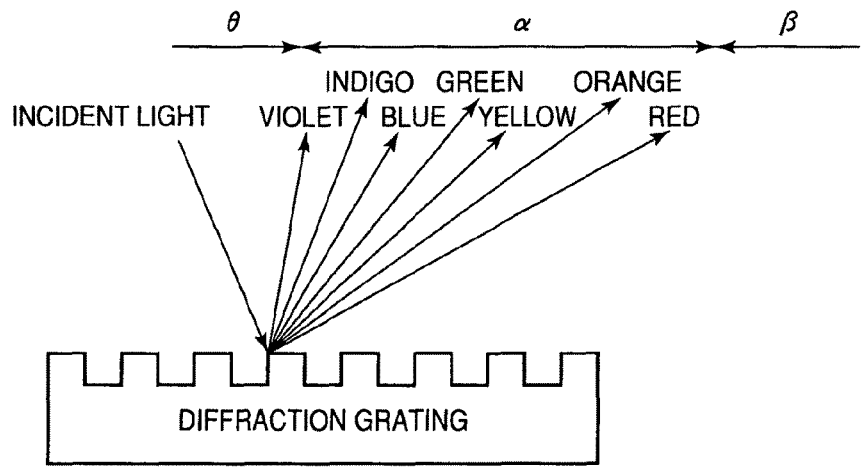
FIG. 9 is an explanatory view showing the relationship between the wavelength and the reflection angle when light that has entered the diffraction grating is reflected.
Figure 10:
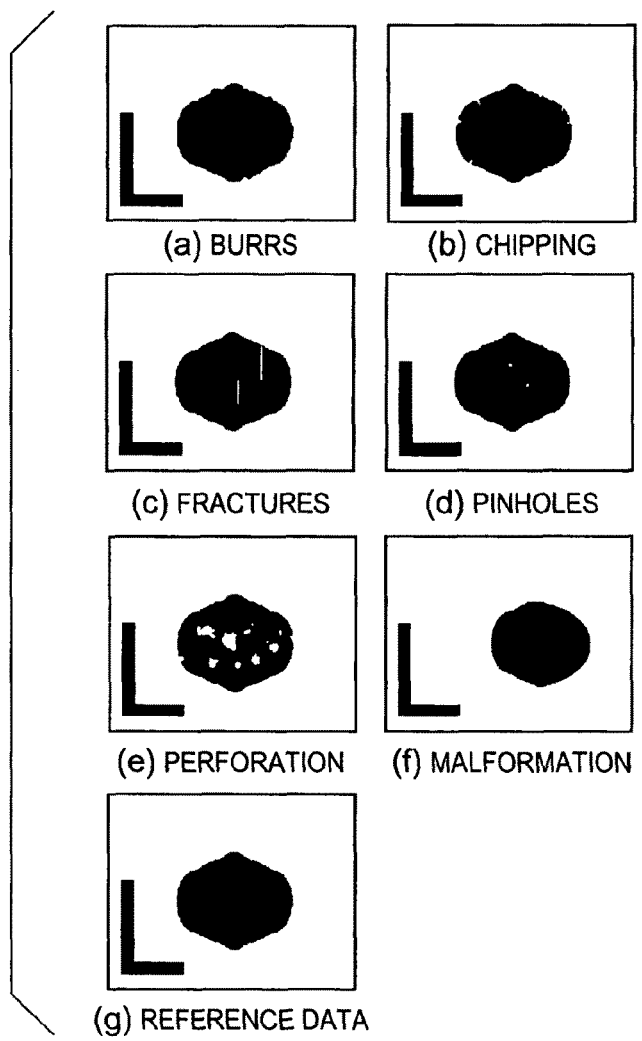
FIG. 10(a) to 10(g) are explanatory views showing examples of binary images representing defects obtained in the embodiment.
Figure 11:
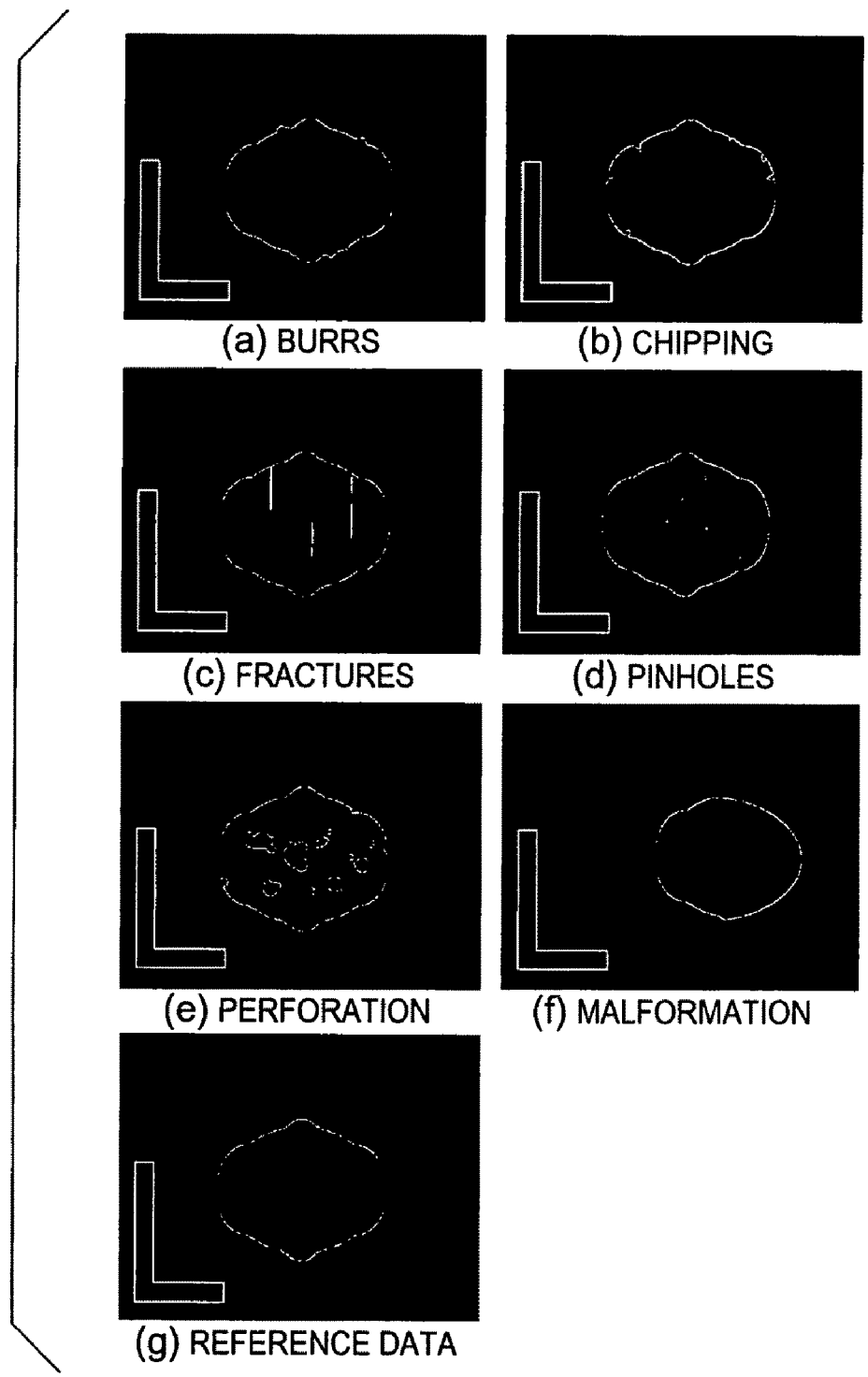
FIG. 11(a) to 11(g) are explanatory views showing examples of images representing the outlines of defects obtained in the embodiment.

If infrared rays irradiate a printed product surface with an OVD, diffuse reflection occurs in all ranges α, β, and θ shown in FIG. 9. Hence, the irradiation angle from the light source and the camera position are set in consideration of the reflection characteristic of the diffraction grating while irradiating the OVD including region of the printed product with the OVD with illumination containing infrared rays from the light source. Then, the image of the vicinity of the region including the OVD is captured.

Let N be the number of trenches per 1 [mm] in the OVD portion where diffraction takes place. To prevent the camera from receiving reflected light with the diffraction wavelength λ [nm] or more, the angle φ made by the irradiation angle of illumination and the light-receiving angle of the camera shown in FIG. 4 must satisfy $$\sin\phi < N\lambda[\text{nm}] \times 10^{-6} \quad (1)$$

for all OVD regions, as described above.

Assume that the number of trenches per 1 [mm] in the OVD is 500, and the wavelength is 750 [nm] or more. When they are substituted into inequality (1), φ<49°. That is, the angle the light-receiving angle of the camera makes with the irradiation angle of the light source is preferably 49° or less with respect to the printed product with the OVD. However, the light source and camera need to be arranged in consideration of the possibility that the camera may receive mirror-reflected light if the angle φ is too small.

For example, the camera for image data acquisition is arranged immediately above the printed product. A filter is attached to the lens portion of the camera. Image data is extracted by irradiating the printed product with illumination containing infrared rays at an angle of 30° with respect to the camera. Since the image data is acquired in the angle range a shown in FIG. 9, the camera receives the infrared rays reflected by the paper surface of the printed product so that bright image data is acquired. However, the OVD is captured as a dark image because it does not reflect infrared rays.

The reflection angle in the range α shown in FIG. 9 changes depending on the inspection target. It is therefore necessary to set the optimum position for each inspection target. The obtained image data is displayed as a monochrome image and subjected to a binarization process as normal image processing. Then, the OVD is extracted as a black image, whereas the paper surface of the printed product is extracted as a white image.

If abnormalities such as chipping or pinholes are present on the edge of the OVD or in it, they are captured white, as shown in FIGS. 10(a) to 10(g) because the infrared rays are reflected even toward the camera, unlike the usual method. When the edge (outline) of the OVD is extracted from the obtained binary image, as shown in FIGS. 11(a) to 11(g), the subsequent process is easy. It is very useful because comparison between the image data and standard image data facilitates determination of the presence/absence of defects. A printed product with defects detected is rejected.

As described above, this embodiment has as its primary object to extract image data to recognize the form after OVD attachment to the printed product. This embodiment does not assume image acquisition to check the change state of the pattern image by the diffraction grating in the OVD. To optically acquire images of an OVD and a printed product with it, a wave range of 650 [nm] or more is used.

In this embodiment, for example, an incandescent lamp is selected as the light source containing infrared rays for the inspection target, i.e., the OVD including region of the printed product with the OVD. Alternatively, the light source is appropriately selected from, e.g., an infrared LED (infrared diode) and an infrared lamp which emit only infrared rays, and a halogen lamp, sunlight, and an HID (High Discharge Lamp) which emit light containing infrared rays.

Light emitted from such a light source and reflected by the region including the OVD contains the visible light range and ultraviolet range which are unnecessary for inspection. Only the infrared range and longer wave range can be extracted by attaching, to the lens portion of the camera, a filter which cuts the visible light range and shorter wave range and transmits the infrared range and longer wave range.

The camera used for image capturing is preferably a CCD area sensor camera or CCD line sensor camera having a high spectral sensitivity in the infrared range. The CCD area sensor camera is suitable for image capturing in so-called offline inspection wherein an inspection target is temporarily taken out from the production line and inspected in a resting state on, e.g., an inspection stage on a table. On the other hand, the CCD line sensor camera is suitable for image capturing in so-called online inspection wherein an inspection target in a running state is inspected on the production line during conveyance through the attachment machine.

The image captured by the camera such as a CCD area sensor camera or CCD line sensor camera is extracted as image data of a two-dimensional image.

The extracted image data is input to the image input means, sent to a memory held in the image processing means, and temporarily stored. The memory stores reference image data of an OVD serving as a standard in advance. Pattern matching with the image data, comparison/determination of the area, or OVD position extraction and comparison/determination is done on the basis of the reference image data, thereby determining the quality related to the form, area, and position of the attached OVD.

Figure 12:
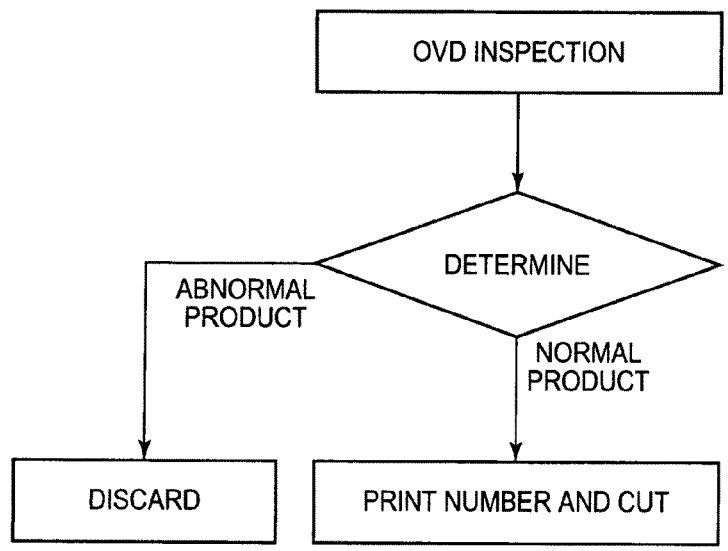
FIG. 12 is a flowchart showing a process of executing OVD attachment inspection according to the embodiment.

The OVD is inspected in accordance with the procedure shown in FIG. 12. If each item falls within the tolerance, the OVD is determined as normal so that the printed product is handled as a normal product. The printed product obtains a number and undergoes, e.g., cutting. If an item falls outside the tolerance, the OVD is determined as defective, so that the printed product is discarded as a defective product.

EXAMPLES

Examples of the OVD inspection apparatus according to the embodiment of the present invention will be described below in more detail with reference to the accompanying drawings. These are merely examples, and the present invention is not limited to them.

Example 1

To inspect a printed product with an OVD in a resting state and check the quality such as the OVD attachment state offline, an OVD inspection apparatus having the arrangement shown in FIG. 3 is used.

The OVD inspection apparatus has, as main components, a light source 2, an image input means 5 including a CCD area sensor camera (to be referred to as a CCD area sensor camera hereinafter) 1 with a visible light cutting infrared transmitting filter and an input unit 10, and an image processing means 6.

Figure 13:
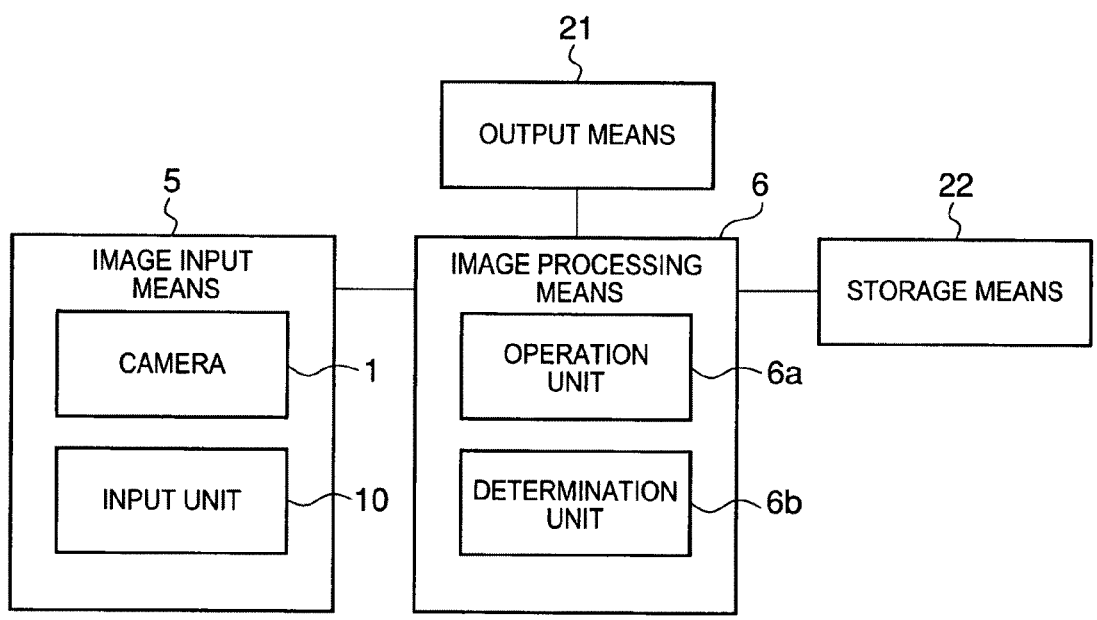
FIG. 13 is a block diagram showing the arrangement of an image input means, image processing means, storage means, and output means included in the OVD inspection apparatus according to the embodiment.

More specifically, as shown in FIG. 13, the image processing means 6 includes an operation unit 6a that executes various kinds of operations, and a determination unit 6b that determines the quality by comparing the image data of an inspection target with reference image data about a standard OVD. The image processing means 6 also connects to a storage means 22 for storing reference image data given in advance and the given image data of an inspection target, and an output means 21 for displaying an image or outputting a warning upon receiving a comparison/determination result.

A printed product 3 as an inspection target with an OVD 4 is fixed on an offline inspection stage. As the light source 2 of irradiation, an incandescent lamp capable of emitting light containing infrared rays is used. The light source 2 is set to an irradiation angle of 30° with respect to the CCD area sensor camera 1.

The CCD area sensor camera 1 has a filter to cut (shield) a wave range shorter than 750 [nm] and transmit a wave range of 750 [nm] or more as shown in FIG. 7. The CCD area sensor camera 1 and the light source 2 relative to the attached OVD are preferably arranged such that diffracted light from the OVD 4 does not enter the CCD area sensor camera 1.

The installation angle of the CCD area sensor camera 1 and light source 2 with respect to the OVD 4 is set such that the irradiation angle becomes, e.g., 30° to prevent the lens of the CCD area sensor camera 1 from receiving infrared rays reflected by the OVD 4 on the printed product 3 with the OVD 4. Any angle other then 30° can be set if it prevents mirror-reflected light from entering the camera 1.

Figure 14:
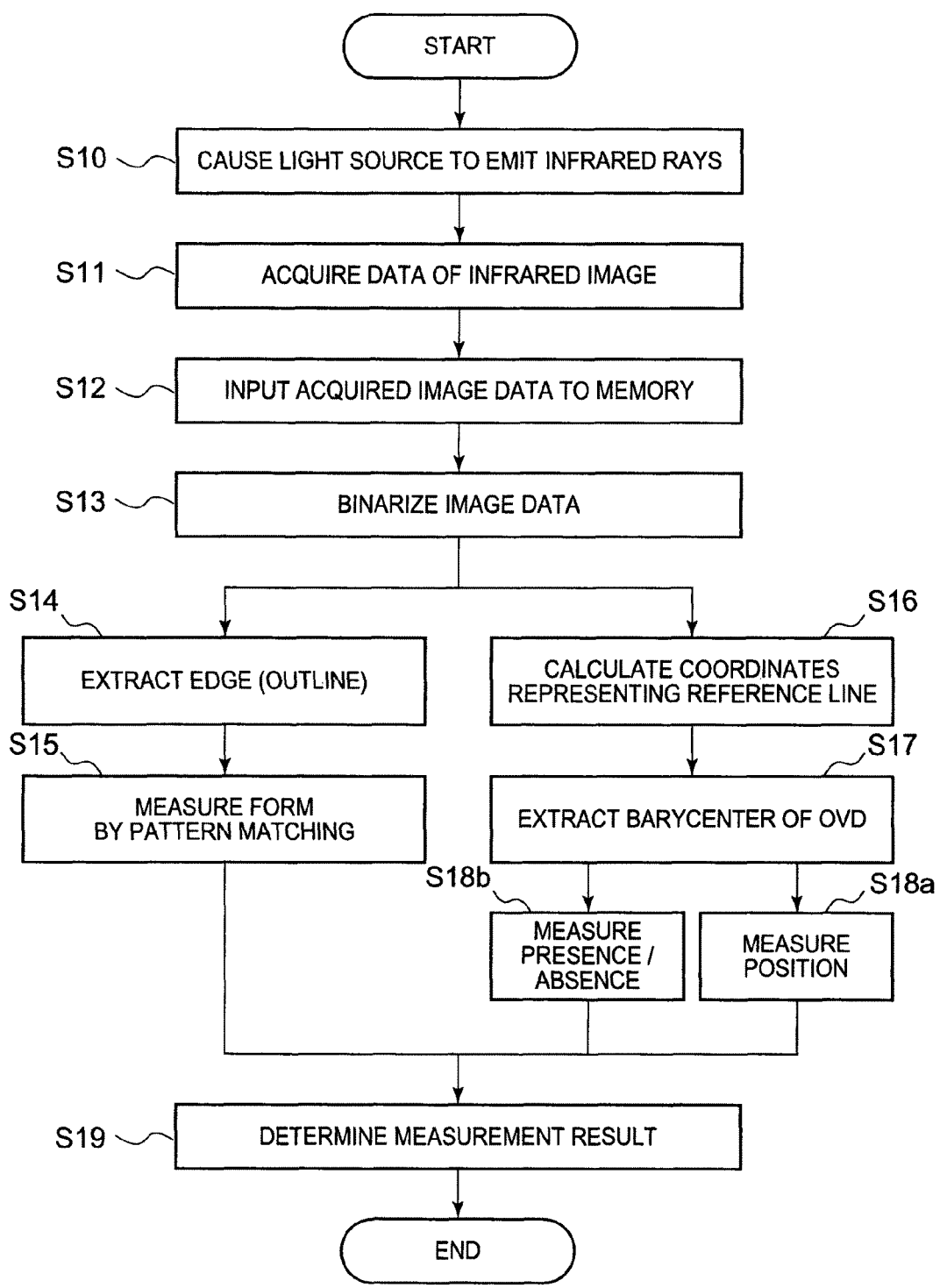
FIG. 14 is a flowchart showing a process of inspecting an OVD offline according to the embodiment.

The OVD inspection process of the OVD inspection method and apparatus according to Example 1 will be described with reference to the flowchart in FIG. 14.

The printed product 3 as the inspection target with the OVD 4 is irradiated with light containing infrared rays from the light source 2 (S10).

As the irradiation light, light containing infrared rays, and more preferably, light in the near infrared range of 750 [nm] to 1,100 [nm] suffices. An infrared lamp that emits only light in the infrared range is more preferable, though the infrared lamp is expensive. A more inexpensive and versatile light source such as an incandescent lamp may be used in consideration of the cost. In this case, unwanted light components can be removed when the camera 1 acquires light transmitted through the visible light cutting infrared transmitting filter. This provides a wide choice of light sources. Hence, any light source capable of emitting light containing infrared rays can be used without any problem even when the visible light range shorter than 750 [nm] and other wave ranges are included.

The CCD area sensor camera 1 captures the light in the infrared range reflected by the printed product 3 irradiated with the infrared rays and acquire image data (S11). The image data of the region including the OVD 4 which is acquired by the CCD area sensor camera 1 is input to the image input means 5.

The CCD area sensor camera 1 has a high spectral sensitivity in the infrared range. The effective sensitivity falls within the wave range from 400 [nm] to 1,000 [nm], and the peak spectral sensitivity falls within the wave range from 600 [nm] to 800 [nm], as shown in FIG. 5.

The CCD area sensor camera 1 acquires the image data of the region including the OVD 4. The acquired image data is a monochrome image as shown in FIGS. 8(c) and 8(d). Even when the angle slightly changes due to, e.g., distortion or bending of the printed product 3, it is possible to acquire the form of the OVD 4 without any influence.

The acquired image data is input to the memory (S12). The image processing means 6 binarizes the image data (S13) to process the monochrome image data into binary data. When the edge (outline) of the OVD 4 is extracted from the processed binary data (S14), binary data of the OVD region is obtained. This makes it possible to reduce the amount of operation data and speed up operations in the subsequent process (e.g., form measurement by pattern matching).

A pattern line is preferably printed on the boundary between the OVD 4 and the print surface by using ink capable of passing infrared rays because the infrared rays reflected to the paper surface are captured as a white image so that boundary extraction is facilitated.

The operation unit in the image processing means 6 compares the data binarized in step S14 with reference image data stored in advance (S15).

The reference image data contains reference image data of the OVD of a base material with a standard OVD and the reference data of a reference mark serving as a reference position. In the comparison process, the binary data of each of the reference image data, the reference data of the reference mark, and the image data of the inspection target is segmented into n×m pixels (n and m are integers; n≧1, and m≧1). Then, the image data are compared with each other. The form is confirmed by pattern matching. Determination is done for each target pixel. When the matching rate is 90% or more, the OVD is determined as an acceptable product. The matching rate and the area per pixel can be set to desired values.

After the binarization process in step S14, position measurement for attachment position inspection is executed in parallel to form inspection by using a predetermined pattern printed in advance by an infrared absorbing ink on the printed product 3 near the attachment position of the OVD 4. This pattern serving as a reference position is a reference mark 14.

Figure 15:
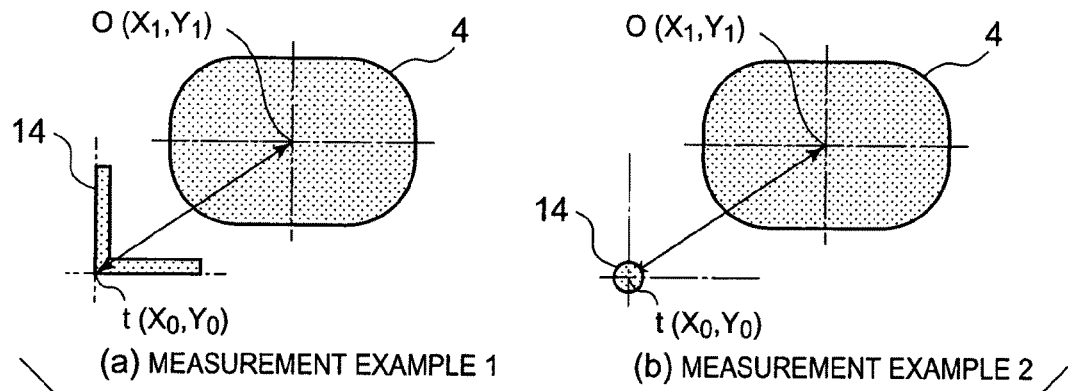
FIGS. 15(a) and 15(b) are explanatory views showing a method of measuring an OVD attachment position according to the embodiment.

When the image of the reference mark 14 is captured, image data of the OVD 4 and reference mark 14 are acquired as shown in FIG. 15(a) or 15(b). For position measurement, coordinates t representing the reference mark 14 are obtained (S16). The coordinates t representing the reference mark 14 only need to specify the reference mark 14. The singular point t as shown in FIG. 15(a) or the barycenter t as shown in FIG. 15(b) can be used.

A barycenter O of the OVD 4 contained in the image data is calculated. On the basis of the coordinates t (X0,Y0) representing the reference mark 14 obtained by the calculation, the barycenter O (X1,Y1) of the OVD image is calculated and extracted (S17).

Then, position measurement is done by obtaining X1-X0 and Y1-Y0 from the coordinates t representing the reference mark 14 and the coordinate value of the barycenter O of the OVD 4 (S18a). Presence/absence measurement of the OVD 4 is done by executing barycenter calculation in step S17 from the image data that has extracted the OVD 4, calculating the area of the target OVD, and measuring the presence/absence of an OVD (S18b). In this way, the position and attachment state quality of the OVD are inspected.

If it is difficult to print the reference mark on the base material by using an infrared absorbing ink, a position representing the base material, e.g., a corner of the base material may be used as the reference position. Even in this case, it is possible to manage the quality of attachment position by calculating X1-X0 and Y1-Y0 in accordance with the same procedure as described above using the reference mark and comparing them with the reference data.

The attachment state quality inspection including form inspection and position inspection is executed by pattern matching. The image processing means 6 determines the quality on the basis of the inspection results (S19). If it is determined on the basis of the two determination results that the form is not acceptable, for example, a determination lamp indicates it. A known means can be used as the display means.

Example 2

An OVD inspection method and apparatus according to Example 2 of the present invention are applied to online inspection on the production line.

Figure 16:
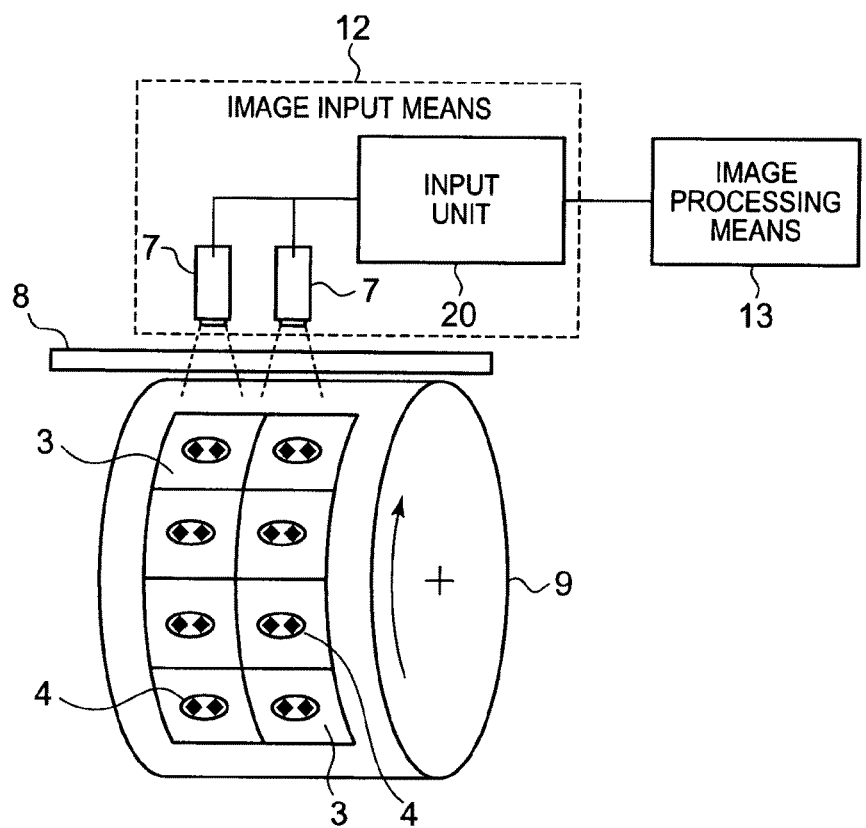
FIG. 16 is a schematic view showing the arrangement of an inspection apparatus for inspecting an OVD online according to the embodiment.

The apparatus for executing online inspection to check the quality including the OVD attachment state of a printed product during conveyance has, as main elements, a linear light source 8, an image input means 12 including a CCD line sensor camera 7 (to be referred to as a CCD line sensor camera hereinafter) with a visible light cutting infrared transmitting filter and an input unit 20, and an image processing means 13, as shown in FIG. 16. An inspection cylinder 9 conveys a printed product 3 as an inspection target with an OVD.

The inspection cylinder 9 can use a known conveyance scheme with, e.g., grippers or a suction system. In Example 2, grippers grip an end of a printing paper sheet, and the rear part of the sheet with respect to the conveyance direction is fixed by a suction system. If the inspection cylinder 9 is not used, a sheet conveyance scheme with a belt conveyor or chain grippers can be used to inspect the printed product 3 as the inspection target with the OVD online during conveyance on the production line. In this case, fluttering of the sheet is preferably minimized.

Figure 17:
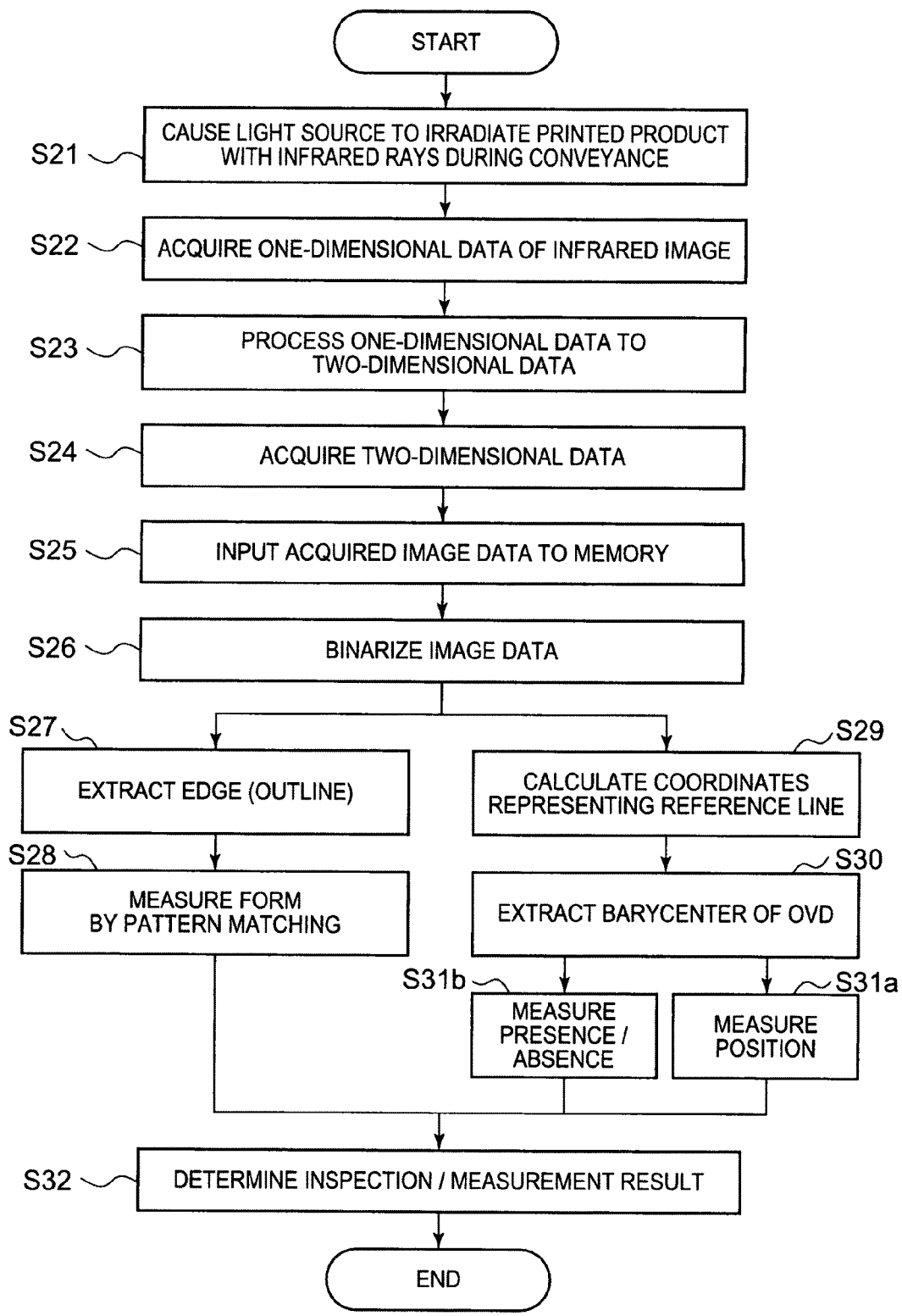
FIG. 17 is a flowchart showing a process of inspecting an OVD online according to the embodiment.

As shown in the flowchart of FIG. 17, the printed product 3 with the OVD, which is conveyed by the inspection cylinder 9, is irradiated with light containing infrared rays from the linear light source 8 (S21). At this time, the irradiation angle is set to 30° with respect to the lens of the CCD line sensor camera 7 due to the same reason as in Example 1.

The CCD line sensor camera 7 repeatedly captures, for each line, an image of light in the infrared range reflected by the printed product 3 irradiated with the light containing infrared rays, thereby acquiring one-dimensional data of an infrared image (S22).

The image input means 12 sequentially inputs, in time series, the one-dimensional image data of the region including the OVD acquired by the CCD line sensor camera 7, thereby generating two-dimensional image data (S23). The CCD line sensor camera used here has a high spectral sensitivity in the infrared range, as in Example 1. The effective sensitivity falls within the wave range from 400 [nm] to 1,000 [nm], and the peak spectral sensitivity falls within the wave range from 700 [nm] to 800 [nm], as shown in FIG. 6. The CCD line sensor camera 7 having the above-described characteristic acquires the image data of the region including the OVD. The acquired image data is a monochrome image, as in Example 1.

The acquired image data is input to the memory (S25). The image processing means 13 binarizes the image data (S26). Extracting the edge (outline) of the OVD from the processed binary data (S27) facilitates the subsequent process.

The operation unit in the image processing means 13 compares the binarized image data with reference image data stored in advance by pattern matching (S28). The reference image data contains reference image data with a standard OVD and the reference data of a reference position, as in Example 1. In this process, the binary data of each of the reference image data, the reference image data, and the image data of the inspection target is segmented into n×m pixels (n and m are integers; $n \geq 1$, and $m \geq 1$). Then, the image data are compared with each other. The form is compared and inspected by pattern matching. Determination is done for each target pixel. When the matching rate is 90% or more, the OVD is determined as an acceptable product. The matching rate and the area per pixel can be set to desired values.

After the binarization process in step S26, position measurement for attachment position inspection is executed in parallel to form inspection by using a reference mark 14 which is printed in advance by an infrared absorbing ink on the printed product 3 near the attachment position of the OVD 4 as a reference position.

For position measurement, a barycenter t of the reference mark 14 is calculated (S29). Next, the OVD 4 is specified from the image data, and a barycenter O is calculated in a similar way. On the basis of the barycenter t (X0,Y0) of the reference mark 14 obtained by the calculation, the barycenter O (X1,Y1) of the OVD image is calculated and extracted (S30). X1-X0 and Y1-Y0 are calculated from the coordinate values of the barycenter t (X0,Y0) of the reference mark 14 and the barycenter O (X1,Y1) of the OVD 4. Position measurement is done on the basis of the numerical values (S31a). The presence/absence of an OVD is determined by executing barycenter extraction from the image data that has extracted the OVD 4, and calculating the area of the target OVD (S31b). In this way, the position and attachment state quality of the OVD are inspected, as in Example 1.

If it is difficult to print the reference mark on the base material by using an infrared absorbing ink, a position representing the base material, e.g., a corner of the base material may be used as the reference position. In this case, it is possible to manage the quality of attachment position by calculating X1-X0 and Y1-Y0 in accordance with the same procedure as described above and comparing them with the reference data.

The attachment state quality inspection including form inspection and position inspection is executed by pattern matching. The image processing means 13 determines the quality on the basis of the inspection results (S32). If it is determined on the basis of the determination results that the form is not acceptable, a determination lamp indicates it, or the printed product is discarded. A known means can be used as the display or discarding means. With the above-described procedure, OVD inspection can be done by almost the same method both online and offline.

Figure 18:
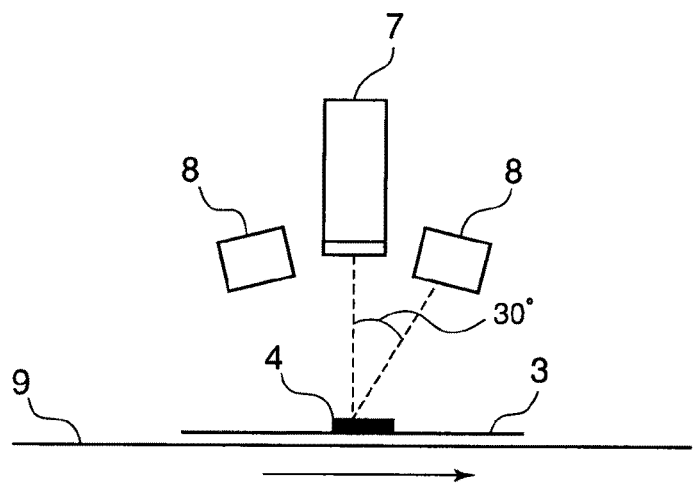
FIG. 18 is a schematic view showing the arrangement of a light source and a camera upon inspecting an OVD online according to the embodiment.
Figure 19:
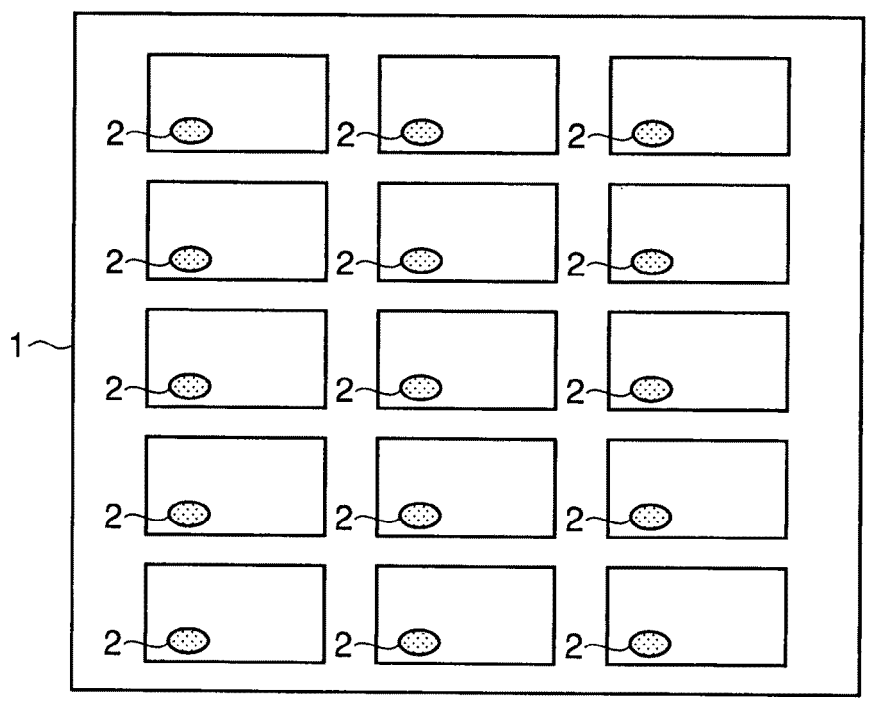
FIG. 19 is an explanatory view showing a printed product by photocomposing to which a plurality of OVDs are attached.

FIG. 18 shows a state wherein the printed product 3 with the OVD 4, which is conveyed by the inspection cylinder 9 in online inspection, is slightly floating from the inspection cylinder 9 or fluttering. Especially when the printed product 3 by photocomposing with a plurality of OVDs 4 as shown in FIG. 19 is conveyed at a high speed, the base material may flutter or undulate during conveyance. Even in this case, according to Examples 1 and 2, the attachment portion of the OVD 4 is extracted by infrared rays. Hence, it is possible to always capture and input stable image data even under these circumstances.

For example, when an OVD is attached to the base material, and a print pattern of an infrared absorbing ink or a pair of print patterns of an infrared absorbing ink and an infrared transmitting ink are formed in a region different from the OVD, the print patterns can be inspected by using the OVD inspection method and apparatus of Example 1 or 2.

It is necessary to register the reference image data of the OVD and/or the data of the print pattern of the infrared absorbing ink in advance. The OVD and print pattern cab be inspected simultaneously by registering the reference image data in advance. Print pattern inspection can be done to check its position, area, and form, like OVD inspection.

The invention claimed is:

1. An OVD inspection method of inspecting an OVD attached to a base material by using an inspection apparatus including illumination means, image input means including image capturing means, storage means, and image processing means, comprising:

arranging the image capturing means and the illumination means at positions where mirror-reflected light and diffracted light from a region of the OVD in a wave range not less than 650 nm have values not more than a threshold value upon a binarization process by the image processing means;

causing the illumination means to irradiate a surface of the base material with infrared rays or light containing infrared rays;

causing the image input means to input image data including a wave range not less than 650 nm from a region including the OVD attached to the base material;

causing the storage means to store, in advance, a first data including reference image data of an OVD serving as a standard, or a second data including the reference image data and reference data indicating a reference position of the OVD serving as the standard; and causing the image processing means to execute the binarization process of the input image data, compare the binarized image data with first data to obtain a first comparison result, or the binarized image data with the second data to obtain a second comparison result, and determine acceptability of at least one of a form, area, and position of the OVD attached to the base material on the basis of the first comparison result or the second comparison result.

2. An OVD inspection method of inspecting an OVD attached to a base material by using an inspection apparatus including illumination means, image input means including image capturing means, storage means, and image processing means, comprising:

arranging the image capturing means and the illumination means at positions where mirror-reflected light and diffracted light from a region of the OVD in a wave range not less than 650 nm have values not more than a threshold value upon a binarization process by the image processing means;

causing the illumination means to irradiate a surface of the base material with infrared rays or light containing infrared rays;

causing the image input means to input image data including a wave range not less than 650 nm from a region including the OVD attached to the base material;

causing the storage means to store outline data indicating an outline of an OVD serving as a standard in advance of receiving the image input data; and causing the image processing means to execute the binarization process of the input the image data, extract the outline data of the OVD attached to the base material from the image data and compare the extracted outline data with the outline data of the OVD serving as the standard, and determine acceptability of a form of the OVD attached to the base material on the basis of a comparison result.

3. An OVD inspection method of inspecting an OVD attached to a base material by using an inspection apparatus including illumination means, image input means including image capturing means, storage means, and image processing means, comprising:

arranging the image capturing means and the illumination means at positions where mirror-reflected light and diffracted light from a region of the OVD in a wave range not less than 650 nm have values not more than a threshold value upon a binarization process by the image processing means;

causing the illumination means to irradiate a surface of the base material with infrared rays or light containing infrared rays;

causing the image input means to input image data including a wave range not less than 650 nm from a region including the OVD attached to the base material;

causing the storage means to store reference data indicating an area value of an OVD serving as a standard in advance of receiving the image input data; and causing the image processing means to execute the binarization process of the input image data, calculate the area value of the OVD attached to the base material from the image data and compare the calculated area value with the area value indicated by the reference data of the OVD serving as the standard, and determine acceptability of an attachment state of the OVD on the basis of a comparison result.

4. An OVD inspection method of inspecting an OVD attached to a base material by using an inspection apparatus including illumination means, image input means including image capturing means, storage means, and image processing means, comprising:

arranging the image capturing means and the illumination means at positions where mirror-reflected light and diffracted light from a region of the OVD in a wave range not less than 650 nm have values not more than a threshold value upon a binarization process by the image processing means;

causing the illumination means to irradiate a surface of the base material with infrared rays or light containing infrared rays;

causing the image input means to input image data including a wave range not less than 650 nm a region including the OVD attached to the base material;

causing the storage means to store, in advance, coordinates representing a position of an OVD and coordinates indicating a reference position to detect the position of the OVD when an OVD serving as a standard is attached to the base material; and causing the image processing means to execute the binarization process of the input input image data, calculate, from the input image data, coordinates indicating a position of the OVD attached to the base material and a reference position to detect the position of the OVD and compare the position of the OVD attached to the base material and the reference position to detect the position of the OVD with the coordinates representing the position of the OVD and the coordinates indicating the reference position to detect the position of the OVD when the OVD serving as the standard is attached to the base material, and determine acceptability of the position of the OVD on the basis of a comparison result.

5. An OVD inspection method of inspecting an OVD) attached to a base material by using an inspection apparatus including illumination means, image input means including image capturing means, storage means, and image processing means, comprising:

arranging the image capturing means and the illumination means at positions where mirror-reflected light and diffracted light from a region of the OVD in a wave range not less than 650 nm have values not more than a threshold value upon a binarization process by the image processing means;

causing the illumination means to irradiate a surface of the base material with infrared rays or light containing infrared rays;

causing the image input means to input image data including a wave range not less than 650 nm from a region including the OVD attached to the base material and a reference mark to detect a position of the OVD;

causing the storage means to store, in advance, coordinates representing a position of an OVD and coordinates representing a reference mark to detect the position of the OVD when an OVD serving as a standard is attached to the base material; and causing the image processing means to execute the binarization process of the input input image data, calculate, from the input image data, coordinates representing a position of the OVD) attached to the base material and a position of the reference mark and compare the coordinates representing the position of the OVD attached to the base material and the position of the reference mark with the coordinates representing the position of the OVD and the coordinates representing the reference mark to detect the position of the OVD when the OVD serving as the standard is attached to the base material, and determine acceptability of the position of the OVD on the basis of a comparison result.

6. An OVD inspection method of inspecting an OVD attached to a base material by using an inspection apparatus including illumination means, image input means including image capturing means, storage means, and image processing means, comprising:

arranging the image capturing means and the illumination means at positions where mirror-reflected light and diffracted light from a region of the OVD in a wave range not less than 650 nm have values not more than a threshold value upon a binarization process by the image processing means;

causing the illumination means to irradiate a surface of the base material with infrared rays or light containing infrared rays;

causing the image input means to input image data including a wave range not less than 650 nm from a region including the OVD attached to the base material and a portion representing a position of the base material;

causing the storage means to store, in advance, coordinates representing a position of an OVD and coordinates representing the base material when an OVD serving as a standard is attached to the base material; and causing the image processing means to execute the binarization process of the input image data, calculate, from the input image data, coordinates representing the OVD attached to the base material and coordinates representing the base material and compare the coordinates representing the OVD attached to the base material and the coordinates representing the base material with the coordinates representing the position of the OVD and the coordinates representing the base material when the OVD serving as the standard is attached to the base material, and determine acceptability of the position of the OVD on the basis of a comparison result.

7. An OVD inspection apparatus for inspecting an OVD attached to a base material, comprising:

illumination means having a light source to irradiate the base material with the OVD with light containing infrared rays;

image input means for inputting image data including a wave range not less than 650 nm from a region including the OVD attached to the base material irradiated with the light containing infrared rays from said illumination means, said image input means including image capturing means which is arranged, relative to said illumination means, at a position where mirror-reflected light and diffracted light from the region of the OVD in a wave range not less than 650 nm have values not more than a threshold value upon a binarization process by image processing means;

storage means for storing, in advance, a first data including reference image data of an OVD serving as a standard or a second data including the reference image data and reference data indicating a reference position of the OVD serving as the standard; and image processing means for executing the binarization process of the input image data, comparing the binarized image data with the first data to obtain a first comparison result, or comparing the binarized image data with the second data to obtain a second comparison result, and determining acceptability of at least one of a form, area, and position of the OVD attached to the base material on the basis of the first comparison result or the second comparison result.

8. An OVD inspection apparatus for inspecting an OVD attached to a base material, comprising:

illumination means having a light source to irradiate the base material with the OVD with light containing infrared rays;

image input means for inputting image data including a wave range not less than 650 nm from a region including the OVD attached to the base material irradiated with the light containing infrared rays from said illumination means, said image input means including image capturing means which is arranged, relative to said illumination means, at a position where mirror-reflected light and diffracted light from the region of the OVD in a wave range not less than 650 nm have values not more than a threshold value upon a binarization process by image processing means;

storage means for storing outline data indicating an outline of an OVD serving as a standard in advance; and image processing means for executing the binarization process of the input image data, extracting outline data of the OVD attached to the base material from the image data and comparing the extracted outline data with the outline data of the OVD serving as the standard, and determining acceptability of a form of the OVD attached to the base material on the basis of a comparison result.

9. An OVD inspection apparatus for inspecting an OVD attached to a base material, comprising:

illumination means having a light source to irradiate the base material with the OVD with light containing infrared rays;

image input means for inputting image data including a wave range not less than 650 nm from a region including the OVD attached to the base material irradiated with the light containing infrared rays from said illumination means, said image input means including image capturing means which is arranged, relative to said illumination means, at a position where mirror-reflected light and diffracted light from the region of the OVD in a wave range not less than 650 nm have values not more than a threshold value upon a binarization process by image processing means;

storage means for storing area data indicating an area of an OVD serving as a standard in advance; and image processing means for executing the binarization process of the input image data, extracting area data of the OVD attached to the base material from the image data and comparing the area data with the area data of the OVD serving as the standard, and determining acceptability of an attachment state of the OVD attached to the base material on the basis of a comparison result.

10. An OVD inspection apparatus for inspecting an OVD attached to a base material, comprising:

illumination means having a light source to irradiate the base material with the OVD with light containing infrared rays;

image input means for inputting image data including a wave range not less than 650 nm from a region including the OVD attached to the base material irradiated with the light containing infrared rays from said illumination means, said image input means including image capturing means which is arranged, relative to said illumination means, at a position where mirror-reflected light and diffracted light from the region of the OVD in a wave range not less than 650 nm have values not more than a threshold value upon a binarization process by image processing means;

storage means for storing, in advance, coordinate data indicating coordinates representing a position of an OVD and coordinates indicating a reference position to detect the position of the OVD when an OVD serving as a standard is attached to the base material; and image processing means for executing the binarization process of the input image data, calculating, from the image data, coordinates indicating a position of the OVD attached to the base material and a reference position to detect the position of the OVD and comparing the position of the OVD attached to the base material and the reference position to detect the position of the OVD with the coordinates representing the position of the OVD and the coordinates indicating the reference position to detect the position of the OVD when the OVD serving as the standard is attached to the base material, and determining acceptability of the position of the OVD attached to the base material on the basis of a comparison result.

11. An OVD inspection apparatus for inspecting an OVD attached to a base material, comprising:
   illumination means having a light source to irradiate the base material with the OVD with light containing infrared rays;
   image input means for inputting image data including a wave range not less than 650 nm from a region including the OVD attached to the base material irradiated with the light containing infrared rays from said illumination means, said image input means including image capturing means which is arranged, relative to said illumination means, at a position where mirror-reflected light and diffracted light from the region of the OVD in a wave range not less than 650 nm have values not more than a threshold value upon a binarization process by image processing means;
   storage means for storing, in advance, coordinate data indicating coordinates representing a position of an OVD and coordinates representing a position of a reference mark to detect the position of the OVD when an OVD serving as a standard is attached to the base material; and
   image processing means for executing the binarization process of the input image data, calculating, from the image data, coordinates representing a position of the OVD attached to the base material and the coordinates of a position of the reference mark and comparing the coordinates representing the position of the OVD attached to the base material and the coordinates representing the position of the reference mark with the coordinates of a position representing the OVD and the coordinates representing the position of the reference mark to detect the position of the OVD when the OVD serving as the standard is attached to the base material, and determining acceptability of the position of the OVD attached to the base material on the basis of a comparison result.

12. An OVD inspection apparatus for inspecting an OVD attached to a base material, comprising:
   illumination means having a light source to irradiate the base material with the OVD with light containing infrared rays;
   image input means for inputting image data including a wave range not less than 650 nm from a region including the OVD attached to the base material irradiated with the light containing infrared rays from said illumination means, said image input means including image capturing means which is arranged, relative to said illumination means, at a position where mirror-reflected light and diffracted light from the region of the OVD in a wave range not less than 650 nm have values not more than a threshold value upon a binarization process by image processing means;
   storage means for storing, in advance, coordinate data indicating coordinates representing a position of an OVD and coordinates representing a position of the base material when an OVD serving as a standard is attached to the base material; and
   image processing means for executing the binarization process of the input image data, calculating, from the image data, coordinates representing a position of the OVD attached to the base material and coordinates of a position representing the base material and comparing the coordinates representing the position of the OVD attached to the base material and the coordinates of the position representing the base material with the coordinates of a position representing the OVD and the coordinates of the position representing the base material when the OVD serving as the standard is attached to the base material, and determine acceptability of the position of the OVD attached to the base material on the basis of a comparison result.

13. An OVD inspection method according to claim 1, wherein said illumination means and said image capturing means are arranged such that
   an angle $\phi$ existing between said illumination means and said image capturing means,
   a wavelength $\lambda$ nm which represents the light emitted from said illumination means, and
   the number N, wherein $N \geq 1$, of trenches per 1 nm in the OVD hold a relationship given by $\sin \phi < N\lambda \text{ nm} \times 10^6$ in the region of the OVD attached to the base material.

14. An OVD inspection apparatus according to claim 7, wherein said illumination means and said image capturing means are arranged such that
   an angle $\phi$ existing between said illumination means and said image capturing means,
   a wavelength $\lambda$ nm which represents the light emitted from said illumination means, and
   the number N, wherein $N \geq 1$, of trenches per 1 nm in the OVD hold a relationship given by $\sin \phi < N\lambda \text{ nm} \times 10.6$ in the region of the OVD attached to the base material.

15. An OVD inspection method according to claim 2, wherein said illumination means and said image capturing means are arranged such that an angle d existing between said illumination means and said image capturing means,
   a wavelength $\lambda$ nm which represents the light emitted from said illumination means, and
   the number N, wherein $N \geq 1$, of trenches per 1 nm in the OVD hold a relationship given by $\sin \phi < N\lambda \text{ nm} \times 10^6$ in the region of the OVD attached to the base material.

16. An OVD inspection method according to claim 3, wherein said illumination means and said image capturing means are arranged such that
   an angle $\phi$ existing between said illumination means and said image capturing means,
   a wavelength $\lambda$ nm which represents the light emitted from said illumination means, and
   the number N, wherein $N \geq 1$, of trenches per 1 nm in the OVD hold a relationship given by $\sin \phi < N\lambda \text{ nm} \times 10^{-6}$ in the region of the OVD attached to the base material.

17. An OVD inspection method according to claim 4, wherein said illumination means and said image capturing means are arranged such that
   an angle $\phi$ existing between said illumination means and said image capturing means,
   a wavelength $\lambda$ nm which represents the light emitted from said illumination means, and
   the number N, wherein $N \geq 1$, of trenches per 1 nm in the OVD hold a relationship given by $\sin \phi < N\lambda \text{ nm} \times 10^{-6}$ in the region of the OVD attached to the base material.

18. An OVD inspection method according to claim 5, wherein said illumination means and said image capturing means are arranged such that
   an angle $\phi$ existing between said illumination means and said image capturing means,
   a wavelength $\lambda$ nm which represents the light emitted from said illumination means, and the number N, wherein N≧1, of trenches per 1 nm in the OVD hold a relationship given by $\sin \phi < N\lambda \text{ nm} \times 10^{-6}$ in the region of the OVD attached to the base material.

19. An OVD inspection method according to claim 6, wherein said illumination means and said image capturing means are arranged such that
- an angle φ existing between said illumination means and said image capturing means,
- a wavelength λ nm which represents the light emitted from said illumination means, and
- the number N, wherein N≧1, of trenches per 1 nm in the OVD hold a relationship given by $\sin \phi < N\lambda \text{ nm} \times 10^{-6}$ in the region of the OVD attached to the base material.

20. An OVD inspection apparatus according to claim 8, wherein said illumination means and said image capturing means are arranged such that
- an angle φ existing between said illumination means and said image capturing means,
- a wavelength λ nm which represents the light emitted from said illumination means, and
- the number N, wherein N≧1, of trenches per 1 nm in the OVD hold a relationship given by $\sin \phi < N\lambda \text{ nm} \times 10^{-6}$ in the region of the OVD attached to the base material.

* * * * *